United States Patent
Stahl

(10) Patent No.: US 7,557,268 B1
(45) Date of Patent: Jul. 7, 2009

(54) PROMOTER FOR EXPRESSION OF A GENE AND RESPONSE TO INFECTION OR WOUNDING

(75) Inventor: Dietmar Jürgen Stahl, Einbeck (DE)

(73) Assignee: KWS SAAT AG, Einbeck (DE)

( * ) Notice: Subject to any disclaimer, the term of this patent is extended or adjusted under 35 U.S.C. 154(b) by 0 days.

(21) Appl. No.: 09/979,303

(22) PCT Filed: May 19, 2000

(86) PCT No.: PCT/DE00/01589

§ 371 (c)(1), (2), (4) Date: Nov. 20, 2001

(87) PCT Pub. No.: WO00/71732

PCT Pub. Date: Nov. 30, 2000

(30) Foreign Application Priority Data

May 21, 1999 (DE) .............................. 199 23 571

(51) Int. Cl.
*A01H 5/00* (2006.01)
*A01H 5/10* (2006.01)
*C12N 15/82* (2006.01)
*C12N 15/11* (2006.01)

(52) U.S. Cl. ........................ 800/301; 800/279; 536/24.1

(58) Field of Classification Search ................ 536/24.1; 800/279, 301
See application file for complete search history.

(56) References Cited

U.S. PATENT DOCUMENTS 5,910,629 A * 6/1999 Strittmatter .................. 800/279

OTHER PUBLICATIONS

Donald et al, 1990, EMBO J. 9:1717-1726.*
Chen et al, 2000, Sex. Plant Reprod. 13:85-94.*
Izawa et al, 1993, J. Mol. Biol. 230:1131-1144.*
Kim et al, 1994, Plant Mol. Biol. 24:105-117.*
Benfrey et al, 1990, Science 250:959-966.*
Eulgem et al, 1999, EMBO J. 18:4689-4699.*
Claudot et al, 1999, Plant Physiol. Biochem. 37:721-730.*
Manners et al, 1998, Plant Mol. Biol. 38:1071-1080.*
Ohme-Takagi et al, 1991, GenBank Accession No. X53600.*
Gurr et al, 2005, Trends Biotechnol. 23:283-290.*
Rushton et al, 2002, Plant Cell 14:749-762.*
Hennig et al, 1993, Plant J. 4:481-493.*
Shah et al, 1996, Plant J. 10:1089-1101.*
Rocher et al, 2005, Gene 344:181-192.*
Rombauts et al, 2003, Plant Physiol. 132:1162-1176.*

* cited by examiner

*Primary Examiner*—Anne R Kubelik
(74) *Attorney, Agent, or Firm*—Patent Central LLC; Stephen A. Pendorf

(57) ABSTRACT

Promoters which increase the pathogen-inducibility of genes in plants, preferably in sugar beets, rape, potatoes, corn, soybeans, wheat, rice, rye, barley, cotton and sunflower. The promoters are characterized in that they lead to the rapid local expression of the gene respectively under the control thereof in different organs and tissues of transgenic plants such as leaves, shoots and/or roots, after having been infected by a pathogen or wounded. This attribute makes these sequences ideal for use as a regulation element for the controlled expression of antifungal compounds and thus for developing fungus-resistant plants.

10 Claims, 15 Drawing Sheets

SEQUENCE LISTING

<110> KWS SAAT AG

<120> NUCLEOTIDE SEQUENCE FOR INCREASING THE DEFENSE REACTION OF
    A PLANT AGAINST INFECTION BY A PATHOGEN

<130> KWS 21.05.99, Update

<140> PCT 0020
<141> 2000-05-19

<150> DE0020
<151> 1999-05-21

<160> 1

<170> PatentIn Ver. 2.1

<210> 1
<211> 5947
<212> DNA
<213> Beta vulgaris

<220>
<221> promoter
<222> (1)..(5947)

<220>
<221> TATA_signal
<222> (5912)..(5915)

<400> 1
aagcttcatc agttctacca gccatgcaaa atattctcaa tgcacttaat tctaacaatt   60
taggtgatca aattaaggtt tctacatccg ttggtacaag cctagtcgaa aacgccttcc  120
caccatctaa tggacaattt ggtaacgttc aatatattac accaataatc aactttataa  180
aacaaaatgg ttcacctttc atggttaata taccctcact ttgcttacca acgtaattca  240
aaacaaattt ctcttgatta cgctttattt acttctcctg gaactgttgt tacggacgat  300
aataatggca gaaattacca aaatttattt gatgcacttg ccgatgcaac atatgcggct  360
ttagataagg ttggtgcgcc cgacgtttca ttgcttacgt ccgagaccgg gtgggcgtca  420
ggcggtggtt tcggggctaa tcacgataat gcaaagaagt atgtcaccaa tttgatcaac  480
catgtgaaga atgggactcc attgaaacca gggagagcaa ttgagacttt cttgtttgcc  540
atgtttgatg aagataagaa accaggggat gaagatgagc ataatttggg gatttttact  600
cctgatcagc agcctaagta tggttcatta aactttaact gattaggctt acaattagct  660
agccaaaagt atggaatttc tagatattgt ttgcaatatg caaatcgtaa cttttcatat  720
caaacgtgta tttgtacttt gtactaccta attaataaga gaatgcgcat tttgttaact  780
tattgagaat gaagtatgct tggaatttag aaatgaagga ttagtatgtg tatcatcaga  840
ccctagctaa ttgaacgtca attaatagtg gcgacaaggg agctacaggc taaaggatg   900
ctatttttctt tttccagggg tacaaggtta ctaattactc cctctgtccc aatttagttg  960

Fig. 1

```
ctacatttgt tttatcacag tttacgagat gcaacaccaa tattttgagt tacatatata 1020
ataaaaatta tatatttgaa aaatacaaat tgggacgaat caaagaagat ccaacatgca 1080
tgactatgtt ttttcttata tatatatatg aagtaaaata tagtcaaagt tatgacgtga 1140
atagtgccta cgatcaaaat gtagcaacta aattgggacg gagggagtag taattatatt 1200
gcacatatca catatgtgca aaccttccct caatggctca atcatatctc tattacgatg 1260
cctaaaagac ccgtatgtaa tcaatttgca aattattaaa acaaaatgtc attgtcttct 1320
taatgatgaa ataaaatttt aaagttattt tttctaccaa ttatattttc tatatatcaa 1380
cgcatgtatc gggtatggct ctctcatagg ctcacatgct cgtaacaaga tgtcattgtc 1440
ttagtgatca aaaggtgagc caaccgggtt catgccgggc ctccccaaaa aaattgacca 1500
ttagtcgggc tgggccaaat ttcaacacgc tttttgtgcc caaacccgc tttcttaggg 1560
caaaaatgtc gagcttctca ggtcaaaatc cgatcaagtc aaaatttgaa caaaaaaatg 1620
tgttttaggt tgcccaaaac tcaaaagaa tatcgggtcg gaccgggacc aaaaaatttg 1680
tttaagccca ggcattttc aaatggagcc agtctcactc taatcagctc tagtcttaaa 1740
cataaatagg atgtactttc tctaattgac tttgtatttt ttttggttgg gggagggagc 1800
taaagtaaat ttttcaaaaa tataatataa aaattaataa tcttactttc aaaaaaaaaa 1860
aatctccact ttcaaccatt tttccaaaat aattccaatt ttagataata aaataaaatt 1920
cctaactttt gcacgaacct actcaaatag taatatactt cctccatttc ttttaagtga 1980
aatattttc tcttttatgt gaaagtatat ataactttga atttatgtcc atatatatta 2040
atctaatgtg ggttcatggt atatagccga tttaacacac ttcaatttgt ttttgagtaa 2100
ggcccttccc cacctaagaa ctattgcaaa ataatcaaaa actaaaatga tctagaaatt 2160
agaatttttt atgtcaaata ttacaaaaat tatttaaatg accaaaagtc aatatttac 2220
acctaacaat tacaacggtg caagtggaag tatgtgataa taactaagag caacggagg 2280
aattctttat tctaatttct agtaatagat aagaagtgat caaaatgctg taagacctaa 2340
caagtaacaa ccactcaacc gagggaggac tccataagtt atagtcgtcg tcactcatct 2400
ttattatata agccaaggaa ggaggtgtgg tgtcctcttt tgaagtgcct aaaatacct 2460
taatgatcta attaatagaa tgaaaaaaat tacaaaagca aatcatttaa aaattctcat 2520
tccaacttgc catttaaaac aagtttaaaa tgatatatgc atcaaatact tcaatcaaaa 2580
attaaatgga caaaatattt ataccttata aaaaaaagat ggcatacata acgtgcacat 2640
gaaaagtctg aacattcact acctttgata ctctttaatt cagttaaaca aactcattat 2700
ttttgttctt tttgttcaaa attcattcac aaaaaattaa tgttaacaat cattcacaaa 2760
cttttatt tttacatta gtgaattaat atatctaaat tcatctaact gttgaatttt 2820
tcacatttaa gtttaatcat aaataaagta cgaatggagt atctaataga ataacaaatt 2880
ttgaaattaa cgcacgcatc gcgtgcatat gaaggctagt ataacaagaa gtcaagagga 2940
gaacatatta aaacgacttg tgaaattaaa tactttcgtt cctgactaat agttagttgc 3000
gtcgcgagta caatagtact aaataagaca attttgtaga cttttctaaa ttggaggatt 3060
caagaattat tcacaggcgg cacgccacat aatattgttc taattttttt tttttttgtc 3120
attttttcact tttgagatcg attttatgac cgcaaatttc taattataat aattgtatgg 3180
gtataacccca agtatgctag cggacacatc aatatgtccg cgaggattgt acgaggacgc 3240
gatcatgaag catatccata gcaacgcctg agattaattt agtgaagttg tctgacaatt 3300
tggcagtcat ctaataagac aaaaaagagg aatcgttct tattgaggca aatcacaacc 3360
atacacgtgt atgaggatta tgcagtctgt caaatgaata atacttttat gaaaagccca 3420
gtattactat tctgctcgta cactaatttt cttctctctc tactttctct ctctaaacct 3480
ttccggacat aatactaact tgagcgttgg aggggtttc cttgcatccc cctaggatag 3540
tttacgtttg tttccttgca gttattcact agcggacgcg cactcaatcc ttggcggcct 3600
tattgaaggt cgtccactgt tttgcaaccg gaacaataat ataaaattgt tatatatgtt 3660
attatgacct taagagtttt gattttttg atgatagcat aaactatcct tgcatctata 3720
tatcatatat gtatgttcgt atatatgatg cagattatta ttgattactt taaaaagttt 3780
tattggagct caagtttgaa agattgaaga ttgaagagta gttagatttt tctttagta 3840
```

Fig. 1 (cont.)

```
aattgtagaa gtaactaact tggttactat tgccctaaga cctaagtgtt attggtaaaa 3900
ttattatcaa taacataatt aattaagcta tttatatcta gtagtgttag tagtatgaat 3960
aataactata gttatggccg gccccaagac gtattgaagt tagtataaat agactaatgg 4020
tagtaatttc acataatgaa aaagattttc aaaaatatgt tgttctatgg aaaataatct 4080
taattaaaca aaatagtatc tttgttaaat atttgaatct aaaataatac tccctccgtt 4140
tcacaatata aggcacgcac gatgttcgag gtcgaacttt gaccgttaat tactcttaat 4200
ttatgttgat agaaaattat gaaaaataat attattatag tattttttcaa gacgaatcca 4260
acggtataat atttatgatt tttatttatc acatttgaga gatatttgta gtcaaagcaa 4320
attctcgtaa aatataaatg ccttatattt taaaatagag ggagtacctt ttttttgtag 4380
aagttattat ctagtttgtg caaagataat ttactttata aaaggtttga taatgttcta 4440
ctccctccgt ctttttttat ttgctacaag cacttttttca caaagaccaa ggagggagtg 4500
gggaccattg acataaatgg aattaacaaa aaagcaaata ggtaaattgt gggacctatg 4560
tattatatat ggaaacattt acaaaatcaa gaagggagtg atggcaaatt tgtaaataaa 4620
gtgtgggaca tatgtactat atatggaaat atttgcaaat gtagcaaata aattgaaaca 4680
cccctaaatg gtaaaatgta gcaaataaaa aaagacggag ggagtaattg attgagaagc 4740
gtatattaag gagatattta tgtaattttaa ctattataga gagtatttat taggtacaag 4800
aatttgtact ttgattcaac ttggcaacac cattagggga gtccactatt agtgaatttg 4860
gtagatatag atctcgagta gattgaacca cgttaaaaat ctttgtttct tgtttaactt 4920
tatttcattg ttttatttttt tgtatgtatg aatcatgttt caacataatc tcaaaatatc 4980
taatatagtt gaaacatagt acataacaca gtgaacattg ttttacaatc ctttttttttt 5040
tttttgcgtg ataactctaa ccactcaatt tactcctttt ttattaatat attgcaaaat 5100
aacattataa catttactta tatagtcaga ggcgtagata atagtgtgca aggagccaaa 5160
cagcacatga ccccccaaaat atattatttt gaaaatttta ccgaagaaat caccctggtt 5220
tcccaccctt aataaatttg tcaataatct atctttagat tttcaacttt ccttctttag 5280
aactctaacc ttccattttt attttctata aatttaggga gccaattttc atattagaat 5340
cggaacccca aaattttcaa gaggacctgt atgtatatgg tttaagaatg atgtatgggc 5400
aaaattaaac ctcaaaagct aaaaggaata tctagagatg aagagagttt gacaagtaaa 5460
tgagatccta caaacgatac gcgttagtac catgatatgc atcattctct taaaatcata 5520
tgatgcaata cgaagtaaaa gactattaca ccatatagca aggaattaat ataattcatt 5580
ttgacgtgtt agtccttcct gactacaata ctagattaaa ttaggcattc atcaattatc 5640
tagtctttgt aatgatctca atcttccaac tttccacatt taacgtactc actcacaagt 5700
aaagaaaaaa ttagcccaaa acacaagtta agtggctgct atacgaagaa atcttcagt 5760
cataattagc attgaattat gtccataaac gacgttttttt gtttgaaatt ttatcacaaa 5820
acgaccctag tgttggtcat attcgtattt tctttattat tcttgtatca aaattttgaa 5880
ctatagtgta gacttttcaa ctcaattatc ctataaaaac tggtaatatc tatgatgatt 5940
caataaa                                                            5947
```

Fig. 1 (cont.)

AGTC<u>ACTAGT</u> CAAAATTTGA TATTTTTCTC TGTTCTTAGA GTTATTTCTT    50

CACAATGAGG CTAATTAGCA CAACTT<u>CTGC</u> <u>AGGCGGCCGC</u> AGTCA    95
      M    R    L    I    S    T    T    S    A    G    G    R    Q    S

Fig. 5

```
AGTCACTAGT AGAAAATCTA ACTTTGGTTC TCTCTCTCGTT GTCTTTTCCA         50

ACTTCAAAAA TGAAGAATTT GATTTTCCTA ACGATGTTTC TGACTATATT         100
           M  K  N  L  I  F  L  T  M  F  L  T  I  L

ACTACAAACA AACGCCGGCG CGGCCGCACT G                             131
 L  Q  T  N  A
```

*: heavily infected

PROMOTER FOR EXPRESSION OF A GENE AND RESPONSE TO INFECTION OR WOUNDING

The present invention concerns a nucleotide sequence for enhancing the defensive reaction of a plant against infection by a pathogen, as well as gene constructs with such a nucleotide sequence. The invention further concerns a process for enhancing the defensive reaction of a plant against infection by a pathogen, as well as transgenic plants and seeds of these plants.

It is known that plants are liable to infection by various agents or parasites. Herein, cultivated plants are usually more susceptible to a parasite infection than their wild counterparts.

The damage to agricultural crops due to pathogenic infections results annually in a crop loss of up to 50%. Particularly significant are the losses due to infection by fungal pathogens. Frequently fungi are encountered which are chlorophyll free, heterotrophic thallophytes. Their thalli are frequently fibrous and as a rule are surrounded by a cell wall.

Since the employment of fungicides is only possible to a limited extent, it is desirable to induce resistance against fungal pathogens also in cultivated plants. The breeding of tolerant/resistant cultured plants is thus of particular economic significance. Traditional breeding programs are however strongly limited in their ability to introduce foreign genes, and besides this, the investment in time and personal effort is very high.

Developments in plant biotechnology have made it possible to introduce genes in the greater part of the known cultivated plants and to express proteins encoded by the genes.

For the expression of a gene, the selection of a suitable promoter is of substantial importance. Accordingly, there exists a great need for well-characterized promoters with specific characteristics.)

In plants, promoters can have a whole plant activity, an organ specific activity, a tissue specific activity or a cell specific activity, or possess an inducible activity. Whole plant promoters are capable of causing expression, during the normal development of a plant, of an encoded region associated therewith, in all tissues. The expression level must be of equal measure for all tissues and all cell types. Whole plant promoters can be of plant, bacterial or viral origin.

It has been possible in the past few years to isolate a large number of plant promoters and to research their effect. Broad application has in the meantime been found for Octopinsynthase (ocs), Nopalinsynthase (nos) and Mannopinsynthase (mas) isolated from *Agro-bacterium tumefaciens* or, as the case may be, TR-promoters (De Greve et al. 1982, Depicker et al., 1982; Velten et al., 1984) and the 35S-promoter of cauliflower mosaic virus (Odell et al., 1985). Plant promoters with whole plant activity have been described for tobacco (WO 97/28268) and raspberries (WO 97/27307).

Organic, tissue or cell specific promoters can be employed for the expression of genes in specific plant parts. In this context, specificity can mean that the promoter primarily or exclusive is active in one organ, tissue or cell type. Promoters having primary activity in one particular organ are, for example, the tomato promoters TFM7 and TFM9 in tomato fruits (U.S. Pat. No. 5,608,150), a rape promoter in roots (WO 94/02619), a sunflower promoter in seeds (WO 98/45460) and a potato promoter (WO 98/18940) in leaves. These mentioned promoters show their highest activity in the mentioned organs. An exclusive, localized activity for a particular compartment was described for a closing cell specific promoter in the potato (DE 42 07358 A1), for the tapetum specific promoter TA29 in tabacco (EP 0344 029 B1) and for the pistil and pollen specific SLG promoter in *Brassica* (Dzelzkalns et al., 1993).

Inducible promoters are regulatory elements, of which the activity is regulated by endogenous or exogenous stimulants. Endogenous stimulants or triggers could be developmental-dependent processes, phytohormones or critical metabolite concentrations. Exogenous stimuli, which can have an effect on the plant and can activate the promoter, include light, abiotic and biotic stress. Abiotic stress factors include dryness, cold, heat and high salt concentrations in the soil or the mechanical injury of plant parts. Biotic stress situations in the plant are induced by pathogenic infections.

Development-dependent regulating promoters control the development and ripeness of organs or whole plants. The transition from green, photosynthetic active leaves to senescent leaves is, among other things, characterized by the reduction of the promoter activity of genes which are involved in the photosynthesis. These include the promoters for chlorophyll a/b binding protein gene (cab) and the gene of the small subunit of ribulose-1,6-bisphosphatesynthase (ssu). At the same time, the onset of senescence involves the activation of senescence specific promoters.

Beyond this, an organ specific promoter is known, which is active in the storage root tissue of the sugar beet (WO 97/32027). A pathogen active promoter is also described in WO 92/17591.

It is the task of the present invention to provide a further nucleic acid sequence, with the aid of which an improved defense of a plant against pathogens is made possible. This nucleic acid sequence should in particular have an effect against fungal pathogens and protect plants with an age related fungal susceptibility. It is further the task of the present invention to provide a process for enhancing the defensive reaction of a plant against infections by pathogens, as well as the correspondingly improved plants.

The solution of the above listed tasks is inventively accomplished by a nucleotide sequence for elevating the defensive reaction of a plant against pathogen infection, wherein the nucleotide sequence includes at least two different cis-elements, selected from the group of cis-elements consisting of a) L-Box or L-Box like sequences with the hexanucleotide sequence CCTAc/aC b) GCC-Box c) W-Box and possesses the characteristics of a promoteras well as the respective subject of the dependent patent claims. Preferred embodiments of the invention are set forth in the dependent claims.

First, certain concepts and terms used in the specification will be defined, in order to clarify how they are intended to be understood herein.

Regarding promoters, a DNA-sequence is to be understood which controls the expression of a gene under its control depending upon endogenous and exogenous factors. These factors include for example inductors, repressors and similar DNA-binding proteins, as well as environmental influences. The promoter can be comprised of multiple elements. It includes however at least one regulatory element, which is responsible for the transcription of a gene under its control.

Derivatives of a nucleotide sequence are shortened versions of this sequence with the same, modified or singular characteristics as the starting sequence.

Elicitors are substances, which originated in part from the pathogen, in part are released from the plant cell wall by the pathogens. Elicitors from fungi are on the one hand neutral, branched glucans, on the other hand glycoproteins or glycopeptides. Elicitors from the cell walls could be fragments of pectin compounds. Elicitors could cause transcriptional gene expression within 20 minutes, as has been shown for example in the synthesis of PAL-specific mRNA in parsley cell cultures.

Pathogen inducibility means the influence of external factors upon the plant, which has as a consequence the defensive reaction thereof. This includes infections by insects (eating), bacterium, fungi or other pathogens, however also abiotic stimuli such as mechanical wounding (for example by hailstorm).

The pathogen inducibility of the herein described promoter means the elevated transcription of the gene, which is under the control of the promoter, when the pathogen inductor is present and which consequently expresses itself in an active defensive reaction of the concerned plant.

Direct anti-fungal effect means that gene products have a direct anti-fungal effect, in that they, for example, dissolve cell walls or code for phytoalexinsynthases, for example, for metabolites, which adversely impact the fungal metabolism.

Indirect anti-fungal effect means that gene products activate the plant genetic defense. These genes include for example resistance genes, components of the signal transduction (such as kinases, phosphatases), transcription factors or enzymes, which produce the signal substances (such as ethylene forming, salicylic acid forming or jasmonate forming enzymes, reactive oxygen species forming enzymes, nitrogen monoxide forming enzymes).

Age dependency or, as the case may be, developmental dependency is intended to mean the differing intensity of the promoter activation and therewith the expression of the gene controlled by the promoter depending upon the age of the plant.

The term "sink" leaves is intended to refer to leaves which, on the basis of their small size, require more carbohydrates than they themselves produce.

"Source" leaves in contrast are the leaves which, on the basis of their size, produce more carbohydrates then they themselves require.

Infection refers to the earliest point in time, in which the metabolism of the fungus (for example the growth of the fungus) is preparing for a penetration of the host tissue. These include for example the outgrowth of hyphae or the formation of specific infection structures such as penetration hyphae and appressors.

Inoculation refers to the physical meeting of pathogen and host.

The invention will be described in the following in greater detail by reference to the figures and examples:

The inventive nucleotide sequence contains at least two different cis-elements, selected from the following groups
 a) L-Box or L-Box like sequences with the hexanucleotide sequence CCTAc/aC
 b) GCC-Box with the core sequence GCCGCC
 c) W-Box with the hexanucleotide sequence TTGACC
 and possess the characteristic of a promoter.

L-Box means a 12 bp encompassing sequence t/aCTc/aACCTAc/aCc/a (SEQ. ID NO: 2) (Lois et al., 1989; da Costa e Silva et al., 1993) wherein t/a or, as the case may be, c/a means that a T or A or, as the case may be, C or A can be present at this position in the sequence. L-Box-like sequence is intended to mean the sequence which contains the hexanucleotide sequence CCTAc/aC and corresponds in at least one further nucleotide with the L-Box. L-Box or, as the case may be, L-Box-like sequences have been identified in the promoters of the phenylalanine-ammonium-lyase-(pal)-gene of parsley, beans and *arabidopsis thaliana* and certain further genes of the phenylpropane-metabolism pathway (Lois et al., 1989; Ohl et al., 1990). The L-Box was identified by the "in vivo DNA footprinting" technique as a location or source of UV-light and elicitor-inducible DNA/protein interaction. The core sequence CCTAc/aC is the sequence region in which the strongest hypomethylation occurs (Lois et al., 1989). The occurrence of the box L as well as the box P "footprints" occurs contemporaneously with the beginning of the transcription of the pal-gene following UV- or, as the case may be, elicitor-stimulation (da Costa e Silva et al., 1993).

GCC-Box means an 11 bp sequence TAAGAGCCGCC (SEQ. ID NO: 3) (Ohme-Takagi and Shinshi, 1995). GCC-Box also means a nucleotide sequence, which contains only the core motive GCCGCC of the GCC-Box. The GCC-Box determines or relays the activation of promoters through the signal substance ethylene and was described for the promoters of certain pathogen defense genes (Ohme-Takagi and Shinshi, 1995).

W-Box means a hexanucleotide sequence TTGACC. W-Box has also been described in the promoters and other pathogen defense genes (Rushton and Somssich, 1998). The meaning of this cis-element for the pathogen inducibility of the promoters was proved for the corn gene PRms (Raventos et al., 1995) and in the parsley gene PR-1-1 and PR1-2 (Rushton et al., 1996).

The present invention is based upon a recognition that effective nucleotide sequences are obtainable for pathogen defense by combining at least two of the above mentioned cis-elements.

Further combinations of cis-elements are described below.

In a further preferred embodiment of the invention the nucleotide sequence includes a further cis-element, which is responsible for the induction of the defensive reaction via salicylic acid. This concerns a fragment which is the SAR-element (salicylic acid response element). The SAR-element is preferably in reverse complimentary orientation in close proximity to a W-Box.

A SAR-element with the sequence TTCGACCTCC (SEQ. ID NO: 4) was identified as core sequence of a 76 bp DNA fragment of the PR2-d gene in tobacco (Shah and Klessig, 1996). The 76 bp sized fragment with the SAR-element is responsible for the salicylic acid inducibility of the PR2-d gene. SAR-elements in the sense of the present application are TTCGACCTCC sequences (SEQ. ID NO: 5) inclusive of appropriate consensus sequences. Another SAR-element is the sequence TTCGACCTCG (SEQ. ID NO: 6). This preferably is present in reverse complementary orientation to the transcription start at position 4176-4167 and therewith only 2 bp adjacent to the third W-Box.

Further embodiments of the invention result from particular sequences and combinations of the cis-elements. Preferred is a close coupling of the 10 bp SAR-element to a W-Box. This narrow coupling is possibly responsible for a strengthened salicylic acid inducibility of the promoter. Likewise, the presence of three L-Box like sequences as well as the presence of two L-Boxes in normal and reverse complementary orientation appears to be advantageous for the pathogen inducibility of a nucleotide sequence.

One solution of the above described object is provided in particular by the nucleotide sequence (SEQ ID No. 1) according to FIG. 1. This sequence, and therefrom derived sequences, are suitable promoters with a good pathogen inducibility. Derived sequences include among others homologous sequences with a homology of at least 50%, wherein the homology is primarily to be traced back to the correspondence in the region of the cis-elements.

Herein the expression "homology" means homology at the DNA-level, which can be determined according to known processes, for example the computer supported sequence comparison (S. F. Altschul et al. (1990), Basic Local Alignment search tool, J. Mol. Biol. 215: 403-410).

According to a different embodiment of the invention, derivates of a nucleotide sequence (SEQ ID. NO:1) according to FIG. 1 are produced. Beginning with a sequence according to FIG. 1 a polymer chain reaction occurs with the following primer pairs a) P0/P4480 b) P0/P4047 c) P0/P3017 d) P0/P2661 e) P0/P2339 f) P0/P1889 g) P0/P1777 h) P0/P1777* i) P0/P814 j) P0/P368, wherein

P0 bonds with the sequence ACT GAC CAC CCG GGG TGG ATT TAT TG (from nucleotide position 5941-5947 of SEQ. ID NO:1);

P4480 bonds with the sequence CCG GGT CGA CGC CGG GCC TCC CCA AA (from nucleotide position 1464-1489 of SEQ. ID NO:1);

P4047 bonds with the sequence TCC AAT TGT CGA CAA TAA AAT TC (from nucleotide position 1894-1921 of SEQ. ID NO:1);

P3017 bonds with the sequence TAT AAC AAG AAG TCG ACA GGA GAA CAT ATT (from nucleotide position 2920-2949 of SEQ. ID NO:1);

P2661 bonds with the sequence GTG AAG TCG ACT GAC AAT TTT GGC AGT CAT C (from nucleotide position 3282-3311 of SEQ. ID NO:1);

P2339 bonds with the sequence TTA TTG AAG GTC GAC CAC TGT TTT GCA ACC (from nucleotide position 3600-3629 of SEQ. ID NO:1);

P1889 bonds with the sequence AAT ATG TTG ACC TAT GGA AAA TAA TC (from nucleotide position 4054-4079 of SEQ. ID NO:1);

P1777 bonds with the sequence GTT CGA GGT CGA CCT TTG ACC GTT AAT TAC (from nucleotide position 4164-4193 of SEQ. ID NO:1);

P1777* bonds with the sequence GTT CGA GGT CGA CCT TAG ACT GTT AAT TAC (from nucleotide position 4164-4193 of SEQ. ID NO:1);

P814 bonds with the sequence AGT CAG AGG CGT CGA CAA TAG TGT GC (from nucleotide position 5124-5194 of SEQ. ID NO:1); and P368 bonds with the sequence TAT AAT TCA TGT TGA CGT GTT AGT CCT TCC (from nucleotide position 5570-5599 of SEQ. ID NO:1).

Beyond this, also a secretion of expressed protein in apoplasia can be achieved, in that one fuses the nucleotide sequence transcriptionally with the signal sequence of the apoplaistic invertase-inhibitor from tobacco.

Nucleotide sequences according to this invention can however also be achieved with a nucleotide sequence translationally grown or extended at the 3'-area. Preferably, a translational fusion is carried out with the aid of the nucleotide sequence from the sequence according to FIG. 5.

In accordance with the present invention, transgenic plants can be produced. By the incorporation of the nucleotide sequence in the plant to be modified, the pathogen resistance can be influenced. No pleiotrophic gene effects are to expected. Therewith, the crop yield of the stock material remains undisturbed. The resulting transgenic plants show a higher resistance with respect to pathogens, above all against fungal pathogens. These can originate from the group including Plasmodiophoromycetes, Oomycetes, Ascomycetes, Chytridiomycetes, Zygomycetes, Basidiomycetes, and Deuteromycetes varieties.

With the inventive nucleotide sequences it becomes possible in particular to produce gene constructs in which the gene is a gene for pathogen defense. Preferably the gene is a resistance gene or an anti-virulesence gene.

According to a further preferred embodiment of the invention the gene demonstrates direct or indirect anti-fungal effect.

For example it is possible to transform constructs in plants with a signal sequence containing a promoter from pAnjasek can fused with the T4-Lysozyme gene, which then exhibit an elevated or enhanced pathogen defense reaction, especially against fungal pathogens.

The new nucleotide sequence is further characterized thereby, that it can lead to rapid local expression of the gene under its control in various organs and tissues of transgenic plants, such as leaves, shoots and/or roots after pathogen infection or wounding. This characteristic renders the sequence ideal for a regulator element for the controlled expression of anti-fungal compounds and therewith for development of fungal resistant plants. Corresponding advantages are also produced by the derivatives derived from the above described nucleotide sequences.

The inventive nucleotide sequences are also constitutively active in the secondary roots, the main roots and the petioles of sugar beets. In the leaves of sugar beets these sequences show an age dependence, irrespective of the "sink" or "source" character of the leaves, in particular a stronger age-related activity increase. The new nucleotide sequences are further characterized thereby, that they permit in leaves of transgenic plants with increasing plant age an increased expression of the gene which is under their control. Thereby, exceptional combating of fungus disease of plants is realized, such as in sugar beets which exhibit an age related susceptibility with respect to the pathogen *cercospora beticola*.

This surprising characteristic of an age dependent expression can represent for example in Southern countries a solution for subsequent problems following a fungal infection. For example in Italy, where sugar beet cultivation suffers strongly from *Cercospora* infections, and where early and mid-early types are already harvested in July and August, in order to avoid crop loss due to pathogen infections. Here the promoter disclosed in the present application offers the solution, which can be activated at the point in time of highest danger of infection (July/August). Thus, in these cultivation situations the planting of later varieties can be made possible using transgenic pathogen resistance.

Further, the activity increase of such a promoter in leaves can also be used to improve both the quality as well as the age dependent processing characteristics of plants. This includes for example characteristic such as the reduction of storage losses in the case of stored beets, or a reduction in the formation of damaging nitrogen due to the anti-sense expression of a transporter gene.

Table 2 shows the surprisingly strong occurrence of elicitor inducibility of the promoter. In comparison to the control, the non-transgenic rape type Drakkar, the two transgenic lines show an induction factor of 17.7 or as the case may be 16.9 after elicitation.

For the elicitor inducibility, as elicitor the enzyme polygalacturonase from *Rhizopus* is employed.

As a result of the nucleotide sequence according to the invention, the induction of the defensive reaction against fungal pathogens is already detectable on the first day after inoculation. This surprising characteristic is relevant particularly for the early phase of the infection, since an infection by *Cercospora beticola* begins four days after inoculation.

In its natural environment in sugar beets the new A promoter exhibits, during its first 12 weeks of the plant development, both in the "sink" as well also in the "source" leaves, a low, however steadily increasing activity, which however is not greater than the activity in the other organs (petiole, main and secondary roots). After 12 weeks there is, in non-infected "sink" and "source" leaves, an increase in promoter activity, which exceeds the promoter activity in the remaining organs. This indicates a higher age activity of the above-described promoter in leaves.

The promoter is activated both in beet leaves by beet fungi such as for example *Cercospora beticola* as well also in beet roots by root area damaging agents such as for example *Rhizoctonia solani*.

The increase in activity of the promoter in leaves and in the beet body of sugar beets is correlated with the amount of the fungal damage and the tissue damage. By the employment of the promoter in combination with a suitable gene a curative action can be achieved on the basis of this characteristic. Also, in the case of an already occurred infection, the further spreading of the pathogen can be prevented or minimized.

In preferred manner a gene construct is provided, which is comprised of gene and promoter, wherein the gene is under the control of the promoter. Therein the gene is characterized thereby that it has a direct or indirect anti-fungal activity.

With the aid of such a gene construct an enhancement of the defensive reaction of a plant against pathogen infection can be achieved, when a gene construct is stably established or introduced into the genome of a plant. Therein the gene of interest could already be present in the genome of the plant, if the inventive nucleotide sequence can be integrated at the appropriate position.

According to one embodiment of the process of the present invention, the enhancement of the defensive reaction can be caused by biotic and/or abiotic factors. As an abiotic factor, salicylic acid in particular comes into consideration.

Biotic factors can be a plant pathogen, in particular a fungal pathogen. Fungal pathogens originate from a fungi selected from the group including Plasmodiophoromycetes, Oomycetes, Ascomycetes, Chytridiomycetes, Zygomycetes, Basidiomycetes, and Deuteromycetes.

The person of ordinary skill is aware of processes for regenerating from plant cells, which contain the nucleotide sequence according to the present invention, plant parts and whole plants. For example, processes are described by Fennell et al., Plant Cell Rep. 11 (1992), 567-570; Stoeger et al., Platn Cell Rep. 14 (1995), 273-278; Jaehne et al., Theor. Appl. Genet. 89 (1994), 525-533.

As for the plants to which increased resistance can be imparted in accordance with the present invention, these include practically all plants. In particular, agricultural plants can be produced, which exhibit a resistance against fungal pathogens. This type of resistant agricultural plants is greatly superior to the non-resistant relatives, since they cannot be infected by fungal pathogens and thus are less susceptible to disease. Besides this, this type of resistant agricultural plant exhibits the same level of quality and yield as other, non-resistant agricultural plants. This can be traced back to the fact that, in the insertion of the nucleotide sequence according to the present invention, no DNA sequences are transmitted which encode for undesired characteristics under these conditions.

Suitable plants in the sense of the invention are plants which provide nutrients and raw materials, for example carbohydrate providing plants (in particular wheat, corn, rice, rye, potatoes, barley, oat and millet), oil and fat producing plants (in particular peanut, palm oil, olive, grape and sunflower), sugar producing plants (in particular sugar beets, sugar cane, sugar millet) protein producing plants (in particular strawberries, beans, kicher peas, lentils and soy beans), fiber producing plants (in particular cotton, flack, hemp, jute), pleasure substance providing plants (in particular tobacco, tea and cocoa), wood producing plants (in particular birch, fig, fir, Douglas, pine, larch, Limba, mahogany, beech, oak, cedar), feed material providing plants (in particular Lucerne and feed beets), vegetables (in particular cucumbers, types of cabbage, pumpkin, carrot, paprika, lettuce, spinach, radish and tomato), fruits (in particular apples, pears, cherries, melons, grapes, citrus, pineapple and bananas) and further the rubber plant and ornamental plants. Preferably, the modified plant is selected from sugar beets, rape, potatoes, corn, soybean, cotton, wheat, rice, rye, barley, malt and sunflower. This list is however not to be considered limiting.

The invention is also considered with transgenic plants, which are produced from the inventively modified plants by somatic hybridization or crossing.

BRIEF DESCRIPTION OF THE DRAWINGS

For a fuller understanding of the nature and objects of the present invention reference should be made by the following detailed description taken in with the accompanying drawings in which:

FIG. 1 shows the nucleotide sequence SEQ ID No. 1.

FIG. 5 shows the nucleotide and derived amino acid sequence (SEQ. ID NO: 24) of a synthetic DNA-fragment.

FIG. 8 shows the nucleotide and amino acid sequence (SEQ ID. NO: 25) of the signal sequence of the invertase-inhibitor gene (nt-1-inh1) from tobacco following amplification through the primer Sek1 and Sek2.

FIG. 12 shows the activation of the promoter in sugar beets after infection with *Cercospora beticola* under greenhouse conditions.

EXAMPLES

As shown in FIG. 1, the nucleotide sequence of SEQ ID NO: 1 is shown in the 5'-3' orientation. The position of the overall consensus promoter sequences (CAAT- and TATA-motive), the cis-elements (L-Box similar sequence, GCC-Box, W-Box and SAR-Box) are shown below. The numbering begins with position 1 at the 5' end.

Figure 2:
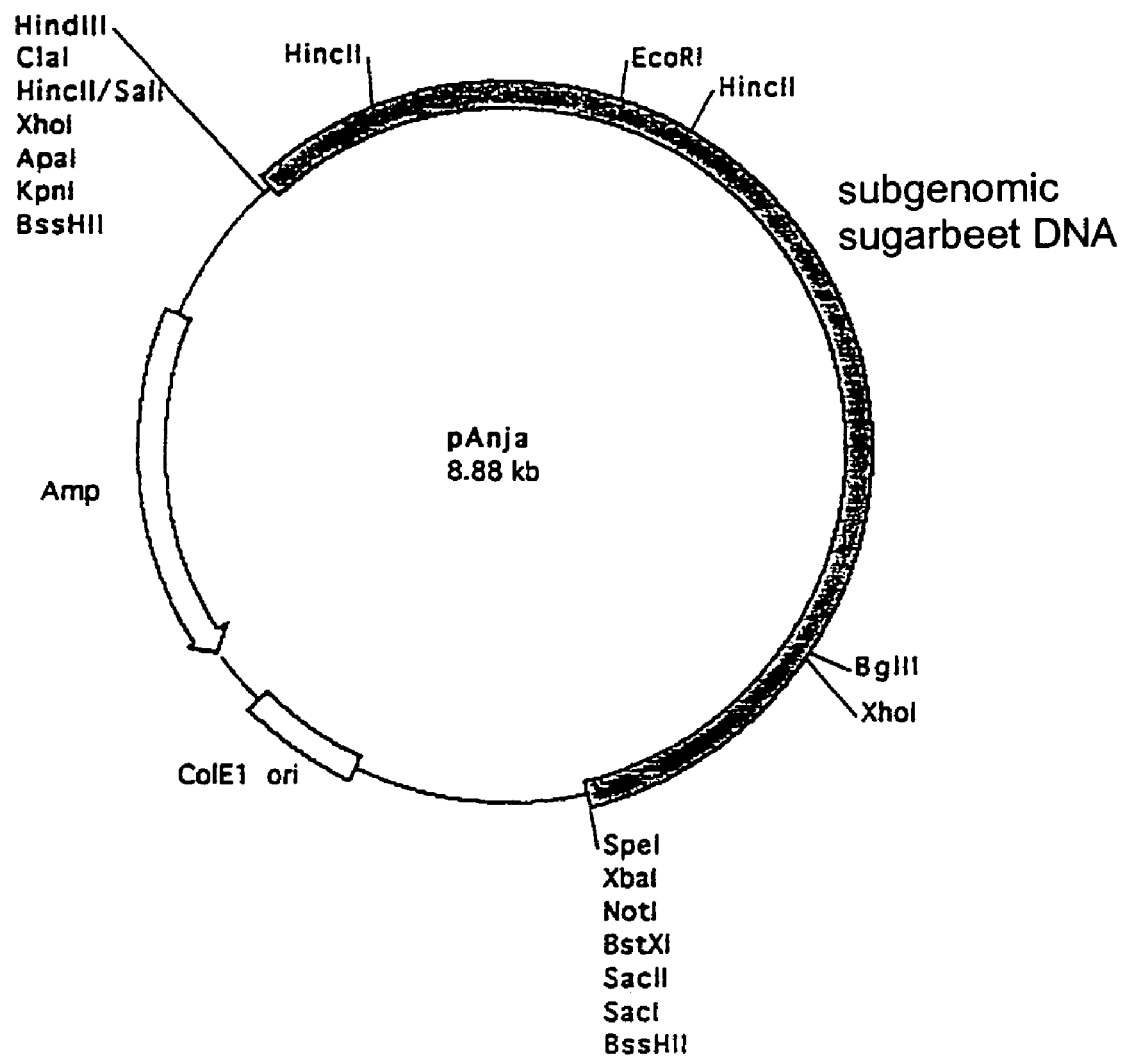
FIG. 2 shows the plasmid pAnja with the 5,947 kb sized geonomic DNA-fragment from sugar beet (*Beta vulgaris*), which was subcloned via HindIII and the blunted Bam-HI restriction point of PBluescriptII KS+ (Stratagene).

The plasmid pAnja with the 5,947 kb sized geonomic DNA-fragment from sugar beet (*Beta vulgaris*), was sub-cloned via HindIII and the blunted Bam-HI restriction point of PBluescriptII KS+ (Stratagene) (FIG. 2). Besides the cleavage points indicated in the sugar beet fragment, further restriction enzymes of the polylinker also cleave in the cloned fragment.

The distribution of cis-elements in the promoter is shown in FIG. 2, in which arrow tips provide respectively the orientation of the cis-elements, wherein the transcription start is at 0.

There is a TATA-Box at nucleotide positions 5912-5915 and a CAAT-Box at nucleotide positions 5903-5906.

There follows at position 4179-4784 a W-Box. Two further W-Boxes are situated at positions 1494-1499 as well as 1586-1581. The W-Boxes at the positions 4179-4184 and 1494-1499 are in normal orientation with reference to the TATA-Box, the W-Box 1586-1581 lies on the complimentary strand in reverse orientation. Only 2 bp removed from the first W-Box, at 4179-4184, there is SAR-Box at position 4176-4167 in reverse complimentary orientation to the TATA-Box. A GCC-Box is twice repeated in reverse complimentary orientation to TATA-Box, at position 3598-3593 as well as at position 3081-3076. An L-Box like sequence lies in three fold repetition at the positions 2331-2342, 2117-2228 and 1916-1927. All three L-Box like sequences lie in same orientation with respect to the TATA-Box.

The shown plasmids (FIG. 4) result from transcriptional combination of the promoter with a gus-gene (pAG4480, pAG4047, pAG3017, pAG2661, pAG2339, pAG1899, pAG1777, pAG1777*, pAG814 as well as pAG368) or as the case may be from restriction digestion (pAG3667, pAG1074, pAG516). These promoter deletions lend themselves for the identification of further cis-elements.

The 95 bp sized DNA-fragment (FIG. 5) carries at the 5'-end the underlined recognition points for the restriction endonuclease SpeI (ACTAGT) and at the 3'-end the underlined recognition points for the restriction endonuclease PstI (CTGCAG) and NotI (GCGGCCGC). The nucleotide sequence at positions 33-81 is identical with the first 22 nucleotides of the non-translated 5'-region and the first 27 nucleotides of the coded region of a β-1,3 glucanase cDNA clone of the sugar beet (Gottschalk and Mikkelsen, 1998).

By removal of a synthetic DNA-fragment (see FIG. 5) behind the transcription start point of the promoter a translatable region is inserted in the vector. The translatable region codes from nucleotide positions 51-95 for the N-terminus of a protein. By use of the recognition points lying in the 3'-region of the synthetic fragment (SEQ ID NO: 24) for restriction endonuclease a fusion protein between the 1.-12. amino acid of a synthetic DNA-fragment and any of various genes to be expressed be produced.

Figure 7:
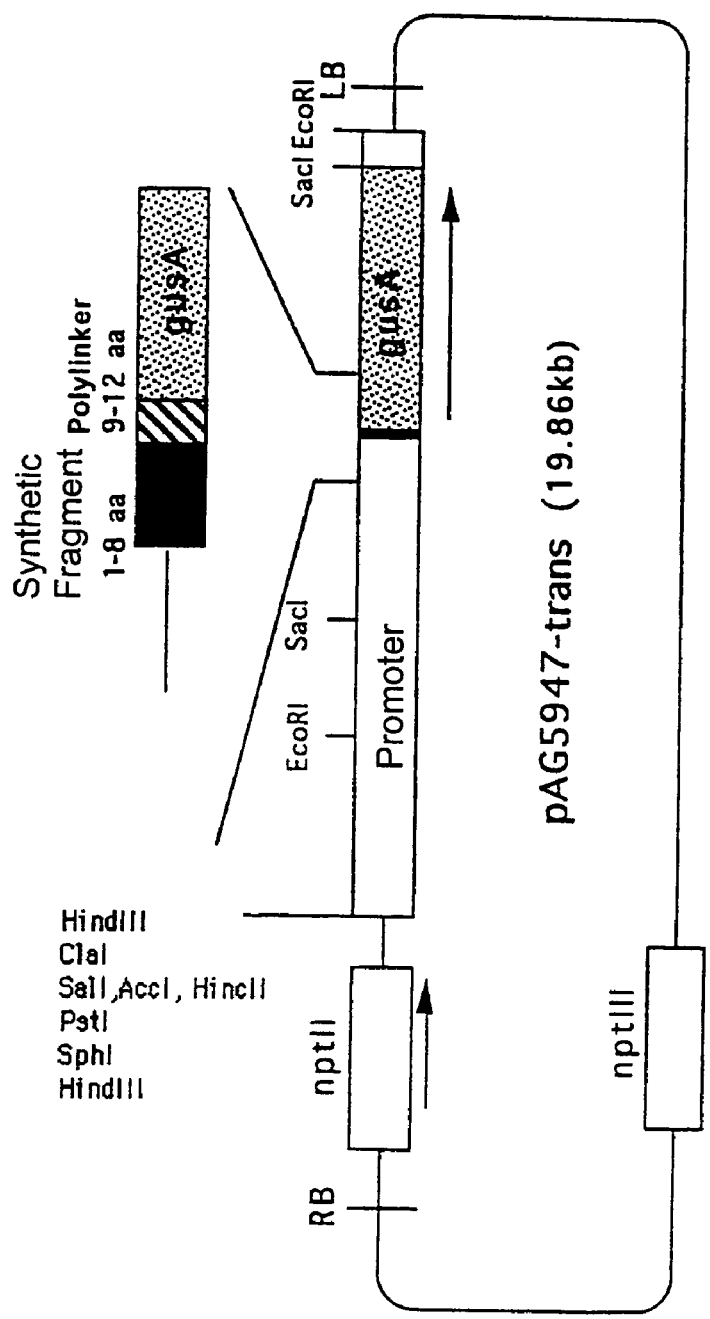
FIG. 7 shows the 19.86 kb sized binary plant transformation vector pAG 5,947-trans.

Within the T-DNA to be transmitted by *Agrobacterium tumefaciens* (limited by the right (RB) and left (LB) border regions, see FIG. 7) lies the section marker nptII and the reporter gene cassette from the promoter and the gus-gene. By sub-cloning the promoter originating from pAnja-PCR-fragment, any desired gene to be expressed can be fused with the signal sequence of the invertase-inhibitor gene.

In leaves of the transformed rape AG-5947-t49, locally 20 μl *Rhizopus* elicitor were pipetted, after an incubation time of 16 hours at 24° C. the GUS-activity can be histochemically verified. The blue coloration of the tissue shows the regions in which high GUS-activity is present (see FIG. 10).

Figure 11:
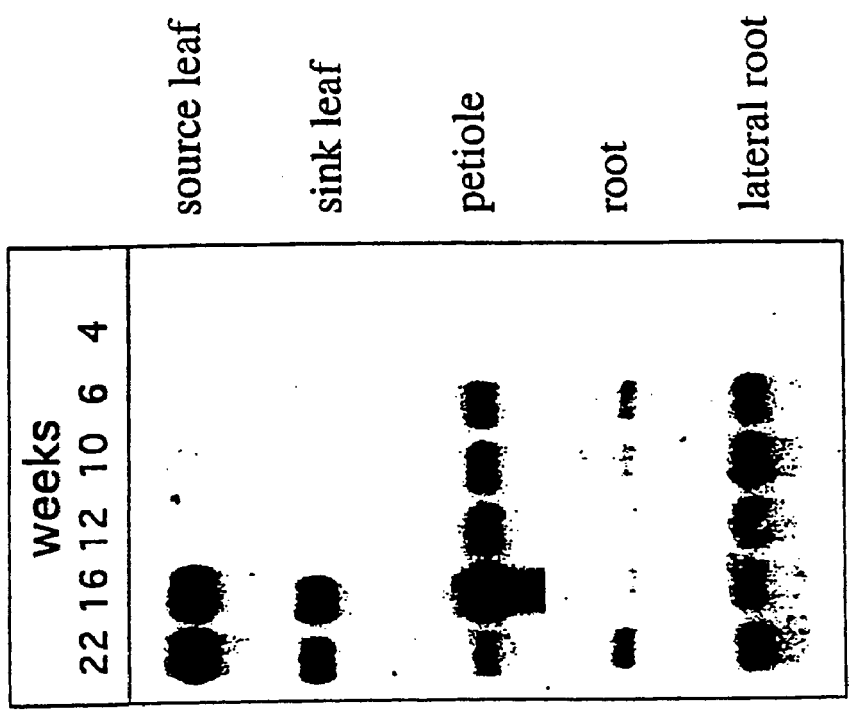
FIG. 11 demonstrates the development dependent promoter activity in a RNA-blot.

Respectively 10 μg total cell-RNA per organ (secondary root, main root, petiole, "sink"-leaf, "source"-leaf) and at time points (4, 6, 10, 12, 16 and 22 weeks after germination) were separated in a denatured formaldehyde agarose gel (FIG. 11).

Figure 12:
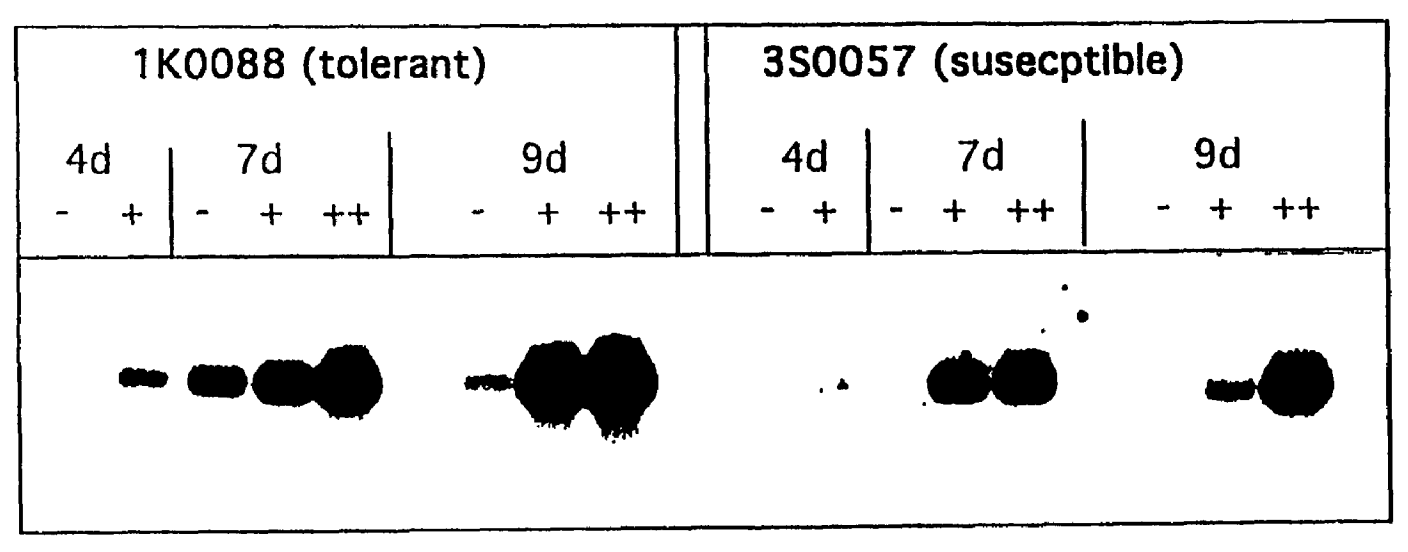

Employed were sugar beets of the tolerant genotype 1K0088 and the susceptible genotype 3S0057. Four, seven and nine days after inoculation leaves were harvested for isolation of the total cell RNA. The activity of the promoter was determined by RNA-blot-analysis (FIG. 12). The damage of the examined leaves due to fungal infection is symbolically represented in the figure: − means healthy control, + means weak damage, ++ means strongly damaged.

Figure 13:
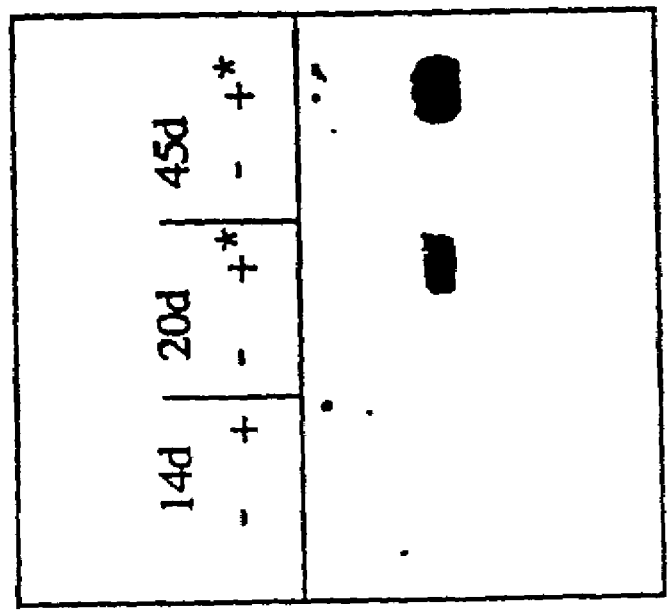
FIG. 13 shows the result of the RNA-blot-analysis for measuring the transcript production in sugar beets of the genotype 1K0088 after infection with the root pathogen *Rhizoctonia solani*.

The fungal infection occurs in a phyto cell, samples for isolation of the total cell RNA were respectively taken 14, 20 and 45 days after inoculation (FIG. 13).

Characterization of the Nucleotide Sequence According to FIG. 1

Figure 3:
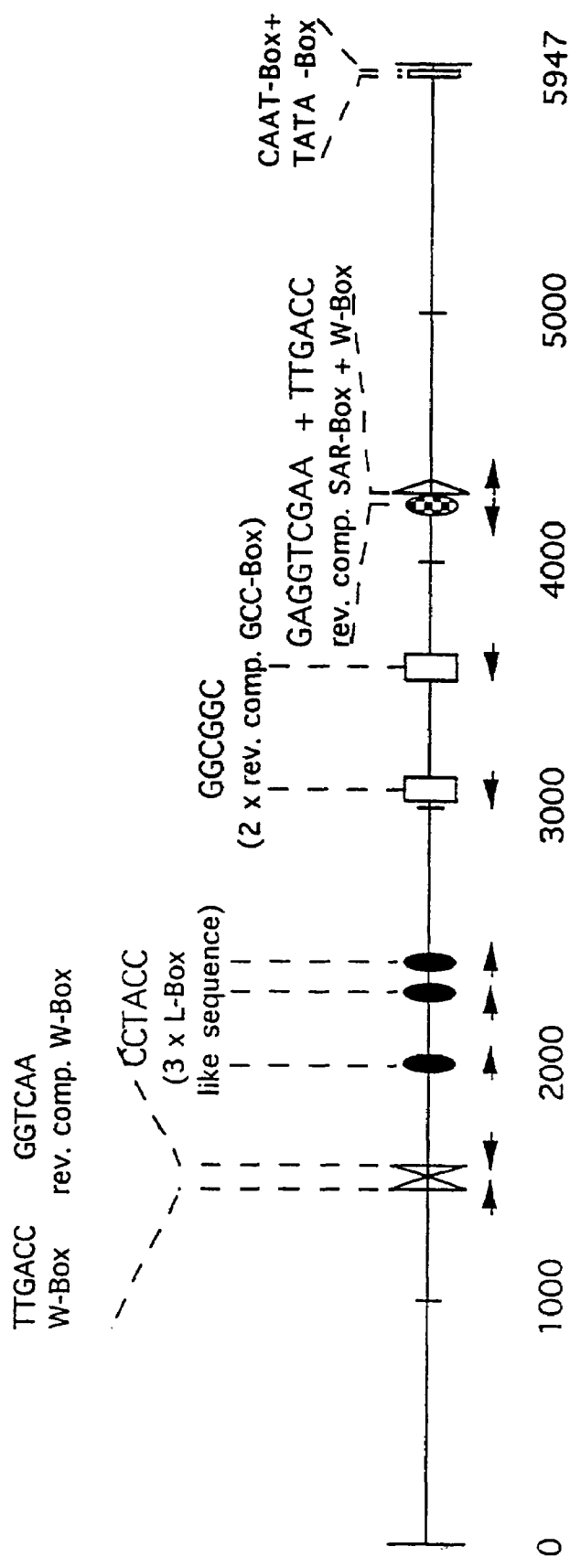
FIG. 3 shows the distribution of cis-elements in the promoter.

The nucleotide sequence of the 5947 bp sized promoter fragment is shown in FIG. 1. The promoter fragment lies sub-cloned in the vector pAnja (FIG. 2). The vector pAnja derives from the plasmid pBluescript II KS+ (Stratagene). The promoter sequence is characterized by multiple cis-elements (FIG. 3), of which the presence and repetition influence the function of the promoter. The L-Box like sequence with the hexanucleotide sequence CCTAAC lies in three repetitions at positions 2331-2342, 2117-2228 and 1916-1927. The L-Box like sequences all have the same orientation in respect to the transcription start and are located within a sequence range of 420 bp.

A further cis-element with the nucleotide sequence GCCGCC, the "ethylene-responsive" or GCC-Box, lies twice repeated in reverse, complimentary orientation to the TATA box at positions 3598-3593 and position 3081-3076. The GCC-Box determines the activation of promoters through the signal substance ethylene and has been described for the promoters of several pathogen defense genes (Ohme-takagi and Shinshi, 1995).

A W-Box with a sequence TTGACC is present three times repeated. The first W-Box extends from positions 1494-1499, the second W-Box in reverse, complimentary orientation from position 1586-1581 and the third W-Box from position 4179-4184. Also characteristic is the presence of the first two W-Boxes, one in normal and one in reverse orientation within a short sequence segment of 92 bp (1494-1586). A third W-Box (4179-4184) lies in close proximity to a further, fourth cis-element, the SAR-element.

Besides the cis-elements, which influence the specific characteristics of the promoter, the promoter obtains the basic nucleotide motive, which each promoter needs for the binding of the basal transcription factors. To this motive belong a CAAT-Box at nucleotide position 5903-5906 and a TATA-Box at nucleotide position 5912-5915.

Derivative of the Nucleotide Sequence According to FIG. 1

Beginning with the vector pAnja, using PCR-techniques or as the case may be with utilization of singular recognition points for restriction endonuclease derivates of the promoter were produced. The cloning process necessary therefore was according to Sambrook et al., 1989. These derivates differed from 5947 bp sized starting promoter in that they are smaller than the starting promoter and do not include all cis-elements, which characterize the starting promoter. By these deletions the promoter fragments exhibit a new activity spectrum, which distinguishes them from the starting promoter. Further, by these deletion preparations, additional, new cis-elements could be identified, which are relevant for the promoter characteristics.

For the production of the promoter deletion fragments by PCR, respectively two oligo-nucleotide primers were employed (Table 1). On the one hand the primer P0 with the sequence ACT GAC CAC CCG GGG TGG ATT TAT TG (SEQ ID. NO: 7) was employed. The primer P0 binds from nucleotide position 5941-5947 of the promoter and the adjacent sequence areas of the multiple cloning points of the vector pBluescriptII KS+. As second primer the oligo-nucleotides P4480, P4047, P3017, P2661, P2339, P1889, P1777, P1777*, P814 or as the case may be P368 were employed, which bind at specific positions within the promoter sequence. The primer P4480 with the sequence CCG GGT CGA CGC CGG GCC TCC CCA AA (SEQ ID. NO: 8) bind from positions 1464-1489. The primer P4047 with the sequence TCC AAT TGT CGA CAA TAA AAT TC (SEQ. ID. NO: 9) binds at position 1894-1921. The primer P3017 with the sequence TAT AAC AAG AAG TCG ACA GGA GAA CAT ATT (SEQ. ID NO: 10) bind from position 2920-2949. The primer P2661 with the sequence GTG AAG TCG ACT GAC AAT TTT GGC AGT CAT C (SEQ. ID NO: 11) bind at position 3282-3311. The primer P2339 with the sequence TTA TTG AAG GTC GAC CAC TGT TTT GCA ACC (SEQ. ID NO: 12) bind from positions 3600-3629. The primer P1889 with the sequence AAT ATG TTC ACC TAT GGA AAA TAA TC (SEQ. ID NO: 13) bind at position 4054-4079. The primer P1777 and P1777* with the sequence GTT CGA GGT CGA CCT TTG ACC GTT AAT TAC (SEQ ID. NO: 14) or as the case may be GTT CGA GGT CGA CCT TAG ACT GTT AAT TAC (SEQ. ID NO: 15) bind at position 4164-4193. The primer P814 with the sequence AGT CAG AGG CGT CGA CAA TAG TGT GC (SEQ. ID NO: 16) bind from positions 5124-5194 and the primer P368 with the sequence TAT AAT TCA TGT CGT GTT AGT CCT TCC (SEQ. ID NO: 17) bind from position 5570-5599.

The PCR conditions for the primer pairs PO/P368, PO/P812, PO/P1777 and PO/P1777* with employment of 1 ng of the plasmid pAnja, a primer concentration of 0.2 µM, 1.5µ Taq-polymerase (Amersham Pharmacia Biotech, Freiburg) and 25 µl reaction volume in a Multicycler PTC-200 (MJ Resaerch, Watertown, USA) are as follows:

| 1  | x | step 1: | 4 min  | 95° C. |
|----|---|---------|--------|--------|
| 30 | x | step 2: | 30 sec | 95° C. |
|    |   | step 3: | 30 sec | 57° C. |
|    |   | step 4: | 2 min  | 72° C. |
| 1  | x | step 5: | 5 min  | 72° C. |

For the primer pairs PO/P4480, PO/P4047, PO/P3017, PO/P2661, PO/P2339 and PO/P1889 the PCR conditions with use of 10 ng of the plasmid pAnja, a primer concentration of 0.2 µM, 1.0 u Advantage KlenTaq-Polyerase-Mix (Clontech Laboratories, Heidelberg) and 25 µl reaction volume in a Multicycler PTC-200 (MJ Resarch, Watertown, USA) are in accordance with the following:

| 1  | x | step 1: | 4 min  | 95° C. |
|----|---|---------|--------|--------|
| 28 | x | step 2: | 30 sec | 95° C. |
|    |   | step 3: | 30 sec | 57° C. |
|    |   | step 4: | 4 min  | 72° C. |
| 1  | x | step 5: | 5 min  | 72° C. |

The use of these PCR-conditions results with the primer pairs PO/P4480 in a 4503 bp sized DNA-fragment. With the aid of the primer pair PO/P4047, PO/P3017, PO/P2661, PO/P2339, PO/P1889, PO/P1777, PO/P1777*, PO/P814, PO/P368 there were amplified 4073, 3047, 2685, 1913, 1800, 1800, 843 and 397 bp sized DNA-fragments. By insertion of a recognition point for the restriction endonuclease SmaI (CCCGGG) in the primer PO and a recognition point for the enzyme SalI (GTCGAC) in the primers P4480, P4047, P3017, P2661, P2339, P1889, P1777, P1777*, P814 and P368 the amplified DNA-fragments could be subsequently cut with the enzymes SmaI and SalI and targetedly cloned in a vector.

The PO/P4480 fragment is cloned as SmaI-SalI fragment in the vector pBluescriptII KS+ cut with SmaI and SalI. The resulting plasmid is assigned, on the basis of the size of the promoter fragment, the identification pA4480 (Table 1). Accordingly the PCR-products PO/P4047, PO/P3017, PO/P2661, PO/P2339, PO/P1889, PO/P1777, PO/P1777*, PO/P814, PO/P368 were cut with SmaI and SalI. Sub-cloned in the vector pBluescriptII KS+ cut with the SmaI and SalI, the resulting plasmids are assigned, on the basis of the promoter size, the identifications pA4047, pA3017, pA2661, pA2339 and pA1889, pA1777, pA1777*, pA814 and pA368 (Table 1).

Transcriptional Combination of the Promoter with a Reporter Gene (Gus-Gene)

Figure 4:
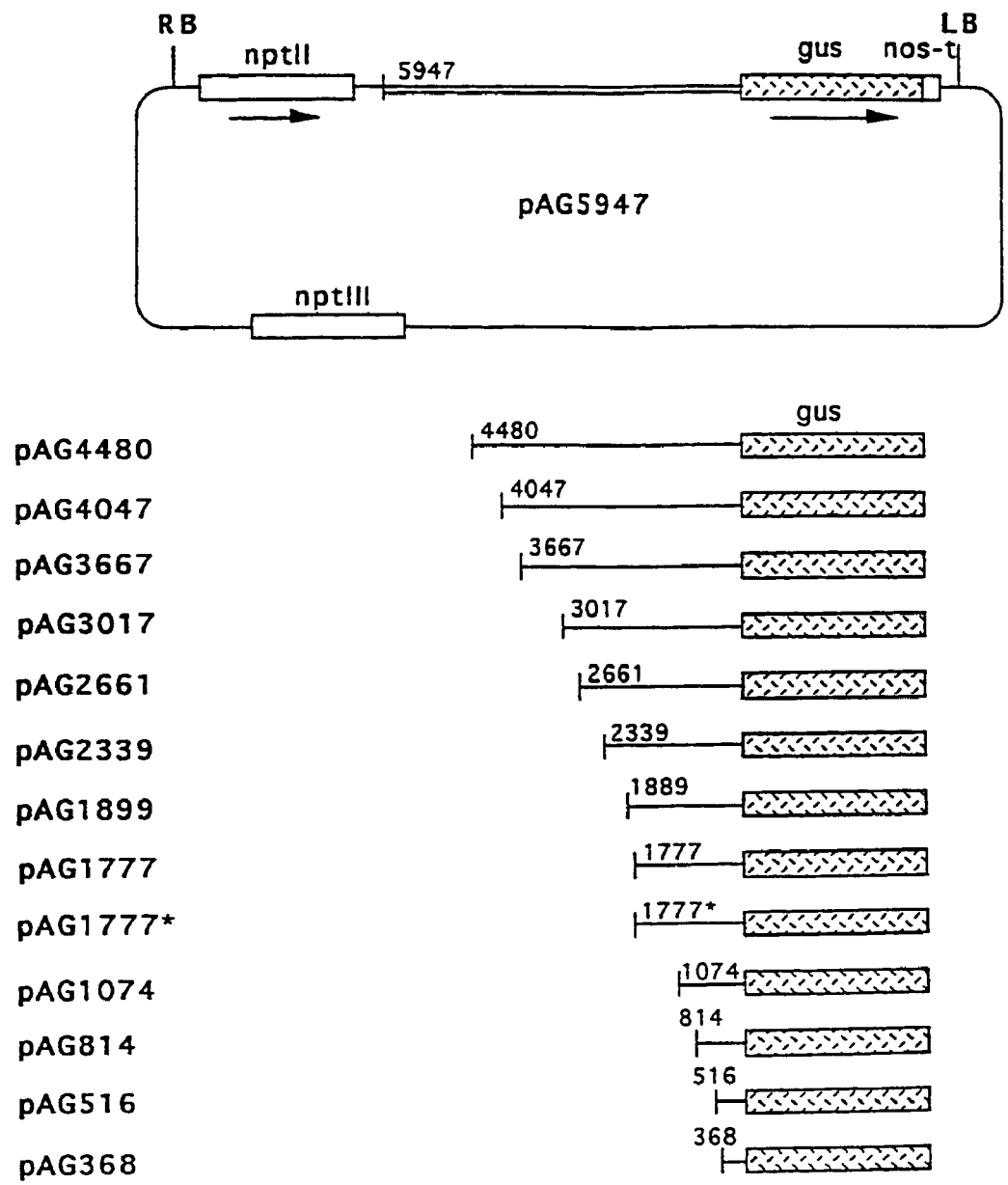
FIG. 4 shows promoter deletions, beginning at sector pAG5947.

Beginning with the plasmid pAnja the 5947 bp sized promoter region was combined as transcriptional fusion with the gus-gene in the plant transformation vector pBI101 (Laboratories, Heidelberg). The resulting vector is assigned identification pAG5947 (FIG. 4). For this the vector pAnja was first linearized with the restriction enzyme SpeI (Boehringer Mannheim) and the resulting DNA-ends were filled according to a Klenow-treatment. By the subsequent SalI-treatment the 5947 bp sized promoter fragment was released and inserted in the vector pBI101 previously treated with SalI and SmaI. According to the described process the deleted promoter fragment from pA4480, pA4047, pA3017, pA2661, pA2339 and pA1889, pA1777, pA1777*, pA814 and pA368 were cloned in the plant transformation vector pBI101. The resulting plasmids were given the identification pAG4480, pAG4047, pAG3017, pAG2661, pAG2339, pAG1889, pAG1777, pAG1777*, pAG814 and pAG368.

Three further promoter deletions were constructed beginning with vector pAG by the use of restriction endonucleases. The vector pAG was cleaved in part by the restriction enzyme SalI and partially with EcoRI, with the enzyme SalI and XhoI and on the other hand with the enzyme SalI and XbaI. By these restriction digestions the promoter region at the sequence from nucleotide 2280-5947, position 4874-5947 and position 5432-5947 was shortened. After the filling of the excised positions by a Klenow treatment the vectors could be ligated and transformed in *E. coli*.

The remaining promoter part after the SalI/EcoRI treatment was 3667 bp sized, after the SalI/XhoI treatment was 1074 bp sized and after the SalI/XbaI treatment was 516 bp sized. The resulting vectors were given identifications pAG3667, pAG1074 or as the case may be pAG516 (FIG. 4).

Modification of the Promoter for a Transitional Fusion with a Reporter Gene (gus-gene)

Figure 6:
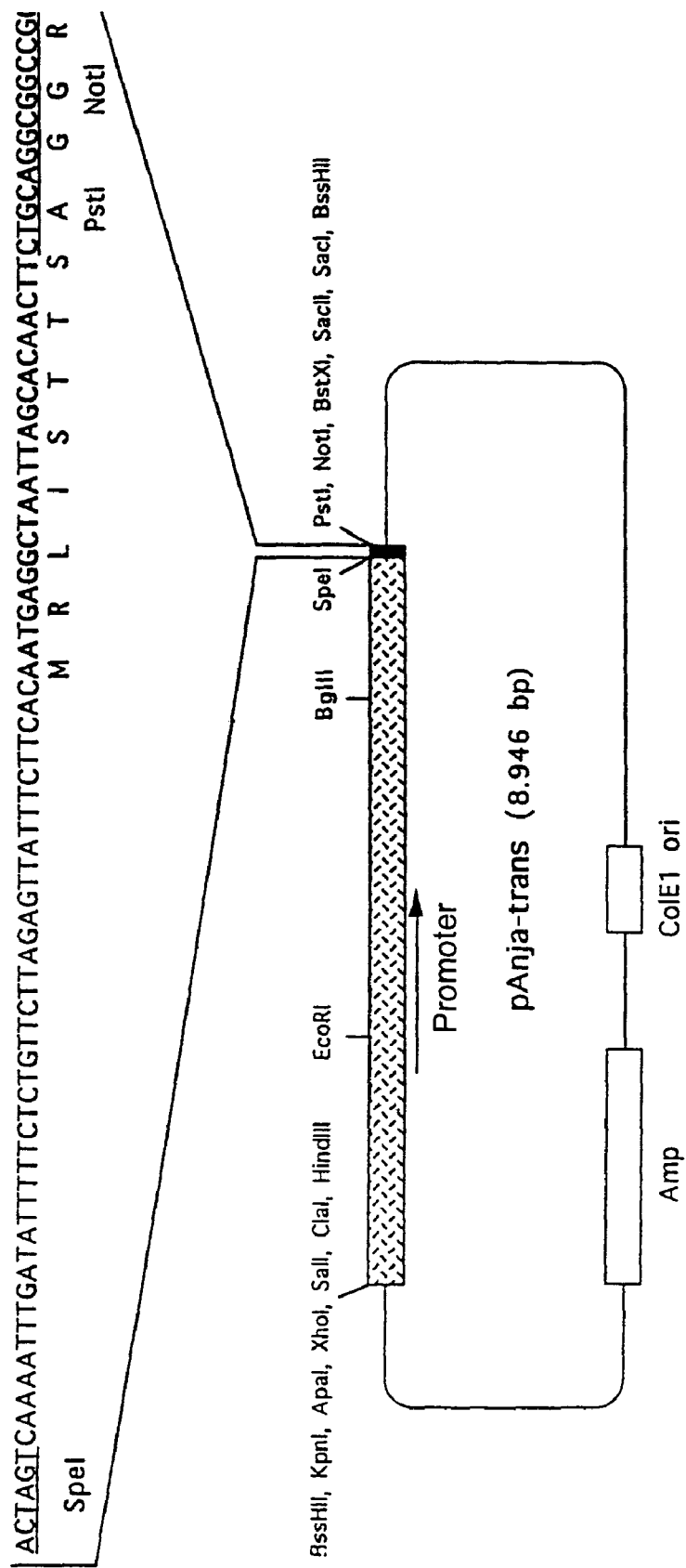
FIG. 6 shows the 8,946 bp sized vector pAnja-trans comprising SEQ ID NO: 24.

In order to combine the described promoter not only transcriptionally but rather also translationally with the gus-gene, a synthetic DNA-fragment (FIG. 5) was cloned in the vector pAnja. The 95 bp sized sequence carried at the 5'-end the recognition point for the restriction endonucleases SpeI and at the 3'-end the recognition point for the enzyme PstI and NotI. The nucleotide sequence coded from nucleotide positions 51-95 for the 5'-end of a protein. The fragment from FIG. 5 was cloned via the SpeI and NotI cleavage points in the vector pAnja. The resulting vector is given the identifications pAnja-tans (FIG. 6).

For the construction of the transformation fusion with the gus-gene the vector pAnja-trans is linearized with the restriction enzyme PstI and the projecting 3'-DNA ends were transformed into blunt ends by T4-polymerase-treatment. The treated vector is again cut with the restriction enzyme SalI and the 6014 bp sized DNA fragment is isolated. The promoter fragment is cloned in the plant transformation vector pBI101, which was previously cleaved with the restriction enzyme SalI and SmaI. By this cloning, the GUS-enzyme obtains a N-terminal elongation of 12 amino acids. While the first 8 amino acids originated from the N-terminus of the synthetic fragment, amino acids 9-12 were coded by the poly-cloning position of vector pBI101. The thus constructed vector carries the identification PAG5947-trans (FIG. 7). Respective translational fusions can also be produced with vectors pA4480, pA4047, pA3017, pA2661, pA2339 and pA1889, pA1777, pA1777*, pA814 and pA368, which subsequently after integration in the plant transformation vector pBI101 are identified with pAG4480-trans, pAG4047-trans, pAG3017-trans, pAG2661-trans, pAG2339-trans, pAG1889-trans, pAG1777-trans, pAG1777*-trans, pAG814-trans and pAG368-trans. Further, beginning with the vector pAG5947-trans, after contacting the construct of pAG3667, pAG1074 and pAG516 with use of the restriction enzyme SalI and EcoRI, SalI and XhoI or as the case may be SalI and XbaI, the deletion constructs pAG3667-trans, pAG1074-trans and pAG516-trans were produced.

Modification of the Promoter for a Secretion of the Expressed Protein in the Apoplast In order to be able, with the aid of the promoter, to also express heterlogous proteins in apoplasts, the 5947 bp sized promoter was transcriptionally fused with the signal sequence of the apoplast invertase-inhibitor from tobacco (Greiner et al., 1998). For this purpose the 106 bp sized 5'-region of the tobacco inhibitor (Nt-inh1) was amplified with the primer Sek1 (AGT CAC TAG TAG AAA ATC TAA CTT TGG TCT CT) (SEQ. ID NO: 18) and the primer Sek2 (CAG TGC GGC CGC GCC GGC GTT TGT TTG TAA TAT AGT CA) (SEQ. ID NO: 19) by PCR from the plasmid pGreiner. The primer Sek1 and Sek2 bind at positions 1-25 or as the case may be 83-106 of the 5'-prime region to be amplified. The total nucleotide sequence of the amplified 131 bp sized fragment is shown in FIG. 8. The amplified 5'-region includes the 49 bp sized non-translated 5'-region of the cDNA-clone and the first 57 bp of the coded region. By the primer sequence Sek1 there is synthesized at the 5'-end of the PCR-product supplementally a recognition point for the restriction endonuclease SpeI (ACTAGT) and by the primer Sek2 at the 3'-end a recognition point for the enzyme NaeI (GCCGGC) and NotI (GCGGCCGC). The PCR-conditions during use of 1 ng of the plasmid pGreiner, a primer concentration of 0.2 µM, 1.5 u Taq-polymerase (Pharmacia) and 25 µl reaction volume in a Multicycler PTC-200 (MJ Research, Watertown, USA Research) are as follows:

| 1  | x | step 1: | 4 min  | 95° C. |
|----|---|---------|--------|--------|
| 30 | x | step 2: | 30 sec | 95° C. |
|    |   | step 3: | 30 sec | 57° C. |
|    |   | step 4: | 2 min  | 72° C. |
| 1  | x | step 5: | 5 min  | 72° C. |

Figure 9:
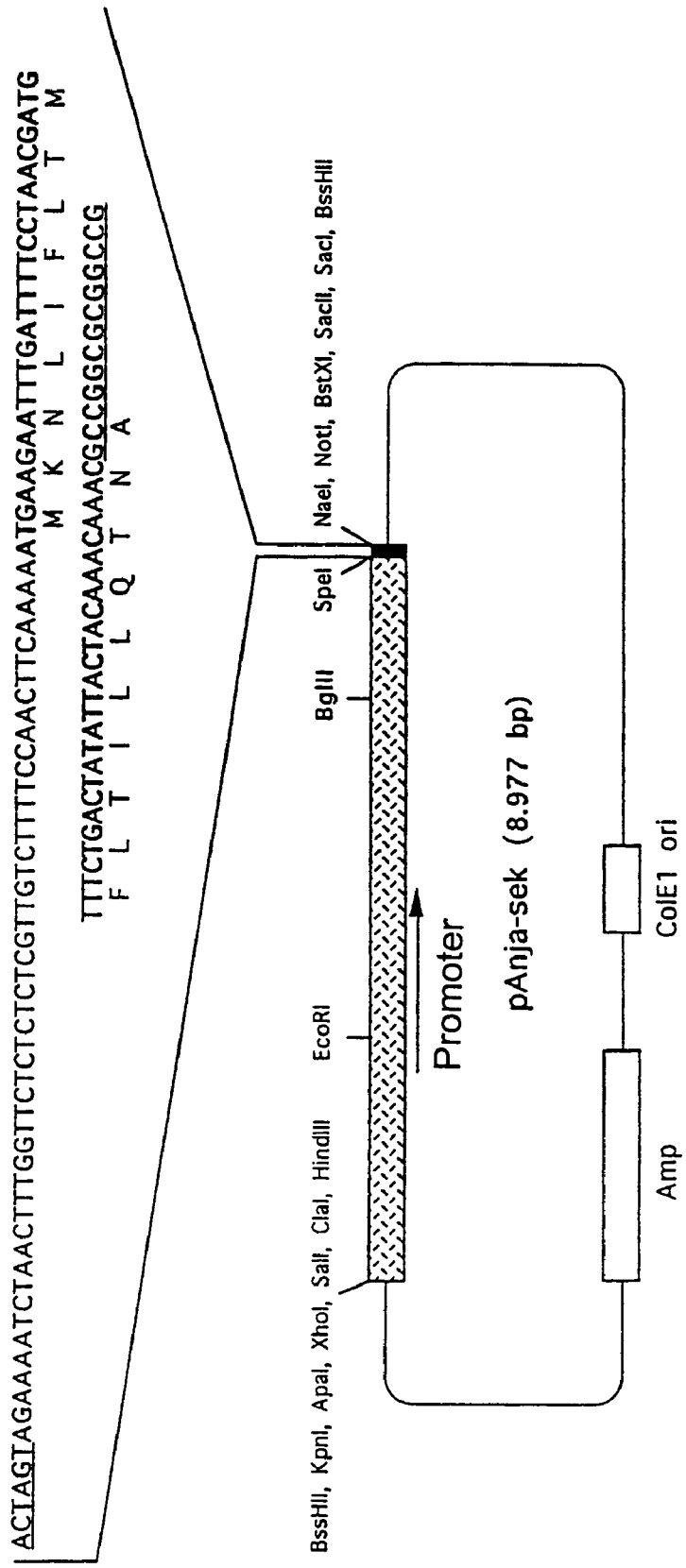
FIG. 9 shows the 8,977 bp sized vector pAnja-sek comprising SEQ ID NO: 25.

After treatment of the fragment with the enzymes SpeI and NotI the fragment was cloned in the vector pAnja linearized with SpeI and NotI. The resulting vector is given identification pAnja-sek (FIG. 9).

The position of the cleavage point by NaeI (GCC/GGC) was so selected, that the GCC-triplet is identical with the triplet of the last amino acid of the signal sequence. By cloning of the gene to be expressed in the NaeI cleavage point of the signal sequence any desired protein with the signal sequence can be fused in a functional manner. After cloning via the appropriate cassette comprised of promoter, signal sequence and gene to be expressed in a binary vector, the construct can be transmitted to plants.

Local, Elicitor Induced Expression of the Promoter in Rape

The constructs provided for the production of transgenic plants were first inserted by a direct DNA-transformation process (An, 1987) in *Agrobacterium tumefaciens* line C58 ATHV. The selection of recombinant *A. tumefaciens* occurred using the antibiotic kanamycin (50 mg/l). In the following the transformation will be described using as example the vector pAG5947-trans. The reporter gene cassette is comprised of the translational fusion between the promoter and the gus-gene and the nos-terminator is transformed with the aid of *A. tumefaciens* according to Horsch et al. (1985) in summer rape of genetype Drakkar. Transgenic plants were selected using the antibiotic kanamycin. The presence of the promoter in the transgenic plants can be verified by PCR. Use of the primer AGATTTTCTTCGTATAGCAGCCAC (SEQ. ID NO: 20) and GTACCATGATATGCATCATTCTCTT (SEQ. ID NO: 21) leads to the amplification of a 269 bp sized DNA-fragment from the promoter representing nucleotide positions 193-461 from FIG. 1. The PCR is carried out with use of 10 ng genometic DNA, a primer concentration of 0.2 µM with an annealing temperature of 50° C. in a Multicycler PTC-200 (MJ Research, Watertown, USA). With use of the described techniques with the binary vector pAG5947-trans, three independent rape transformates were obtained, identified with designations AG5947-t38, AG5947-t48 and AG5947-t49.

Expression Behavior of the Promoter in Transgenic Plants

Elicitor Induction of the Promoter in Leaves, Shoots and Roots of the Transgenic Rape Plants Leaves were removed from the transformates AG5947-t48 and AG5947-t49 as well as the non-transgenic original Drakkar and incubated for elicitor induction in 120 mm sized petri dishes in 50 ml induction medium (LS-medium without sucrose, 5 mM MES pH 6.1, 1 µ/ml *Rhizopus* Pektinase EC 3.2.1.15 of Sigma Chemical Co.) or in control medium (LS-medium without sucrose (Linsmaier and Skoog, 1965), 5 mM MES pH 6.1) for 16 hours at 24° C. The *Rhizopus* Pektinase releases from the plant cell walls pectolytic decomposition products, which for their part have an elicitor effect. The activity of the promoter is determined by a quantitative determination of the β-glucuronidase-(GUS-activity under use of the substrate 4-methyl-umbelliferyl-glucuronid (MUG) according to Jefferson (1987).

The non-transgenic original line Drakkar exhibits as shown in Table 2 in the non-elicited and in the elicited condition a specific glucuronidase activity of 6.68 or as the case may be 6.61 pMol Mu×min$^{-1}$×mg$^{-1}$. The elicitation does not result in any significant change in the glucuronidase activity in the non-transgenic line.

The transgenic lines AG5947-t48 and AG5947-t49 exhibit in the non-elicited condition a specific enzyme activity of 14.0 or as the case may be 138.7 pMol Mu×min$^{-1}$×mg$^{-1}$ and after elicitation a glucuronidase activity of 247.6 or, as the case may be, 1507.9 pMol Mu×min$^{-1}$×mg$^{-1}$. The glucuronidase activity of the transgenic lines is significantly higher, even in the non-elicited condition, than in the non-transgenic line. Under the influence of elicitation there results a 17.6 or as the case may be 16.9 time elevation of the glucuronidase activity and therewith to an induction of the reporter gene. The sugar beet promoter thus shows in leaves of transgenic rape plants an elicitor inducibility and therewith a pathogen inducibility.

In order to confirm, whether the elicitor inducibility of the promoter is available in other plant organs than the leaves, shoot segments and roots were included in the research. For this, F2-plants of the transformates AG5947-t49 were employed under greenhouse conditions. Separated leaves and shoots, which were cut into 5 cm long segments, and cleaned roots were, as already described for leaves, incubated for 16 hours in pectinase containing induction medium or in control medium. In order to be to evaluate the influence of wounding during the sample collection on the measurement result, whole leaves, shoot segments and cleaned roots were immediately frozen subsequent to the sample collection in liquid nitrogen. As shown in Table 4, by the separation of leaves from the plants, the reporter gene activity in the leaves was, in comparison to the control starting level, elevated by the 5.3 multiple and by elicitation supplementally by the 72 fold. The separation and cutting up of the shoot stem resulted in an elevation of the GUS-activity by the 8.3 multiple and by the subsequent elicitation by the 3.5 multiple.

In the case of the root, by the separation of the root a 7.2 multiple and by the elicitation an additional 9 fold elicitor induction of the reporter gene activity was observed. The promoter was activated in transgenic plants in leaves, the shoots and in roots by wounding and additionally by elicitation.

Induction of the Promoter in Leaves of Transgenic Rape Plants by Salicylic Acid and PMG-Elicitors In order to examine the effect of salicylic acid and a purified PMG-elicitor from the cell wall of *Phytophthora sojae* (Valent, 1978) on the promoter activity, leaf disks with a diameter of 14 mm were stamped out of the leaves of greenhouse plants with the aid of a cork punch. The use of leaf disks facilitates the uptake of the salicylic acid or as the case may be the elicitor along the wound edge into the leaf tissue. Respectively 10 leaf disks from leaves of the transformed AG5947-t38 and AG5957-t48 were incubated in 90 mm sized petri dishes in salicylic acid containing medium (LS-medium without sucrose, 5 mM MES pH 7.0, 0.5 mM SA), in PMG-elicitor containing medium (LS-medium without sucrose, 5 mM MES pH 7.0, 25 µg elicitor/ml) or in control medium (LS-medium without sucrose, 5 mM MES pH 7.0) for 16 hours at 24° C. The activity of a promoter is described as in Jefferson (1987) measured by a quantitative determination of the GUS-activity.

As shown in Table 4, for the transgenic lines AG5947-t38 and AG5957-t48 in control medium an enzyme activity of 24.47 or as the case may be 1.86 pMol Mu×Mu×min$^{-1}$×mg$^{-1}$ can be confirmed. The incubation of the leaf disks in the presence of 0.5 mM SA or as the case may be of 25 µg/ml results for the transformate AG5947-t38 to a reporter enzyme activity of 485.3 or as the case may be 187.0 pMol Mu×min$^{-1}$×mg$^{-1}$ and for the transformates AG5957-t48 to an enzyme activity of 17.2 or as the case may be 9.3 pMol Mu×min$^{-1}$×mg$^{-1}$. Therewith the specific glucuronidase activity of the transformate AG5947-t38 is, in comparison to the control starting point, increased by the salicylic acid treatment by the 19.8 multiple and by the PMG-elicitor by the 7.7 multiple. For the transformate AG5947-t38 the induction factor for salicylic acid is 9.2 and for PMG-elicitor it is 5.

Histochemical Evidence of the Local Promoter Activation

Figure 10:
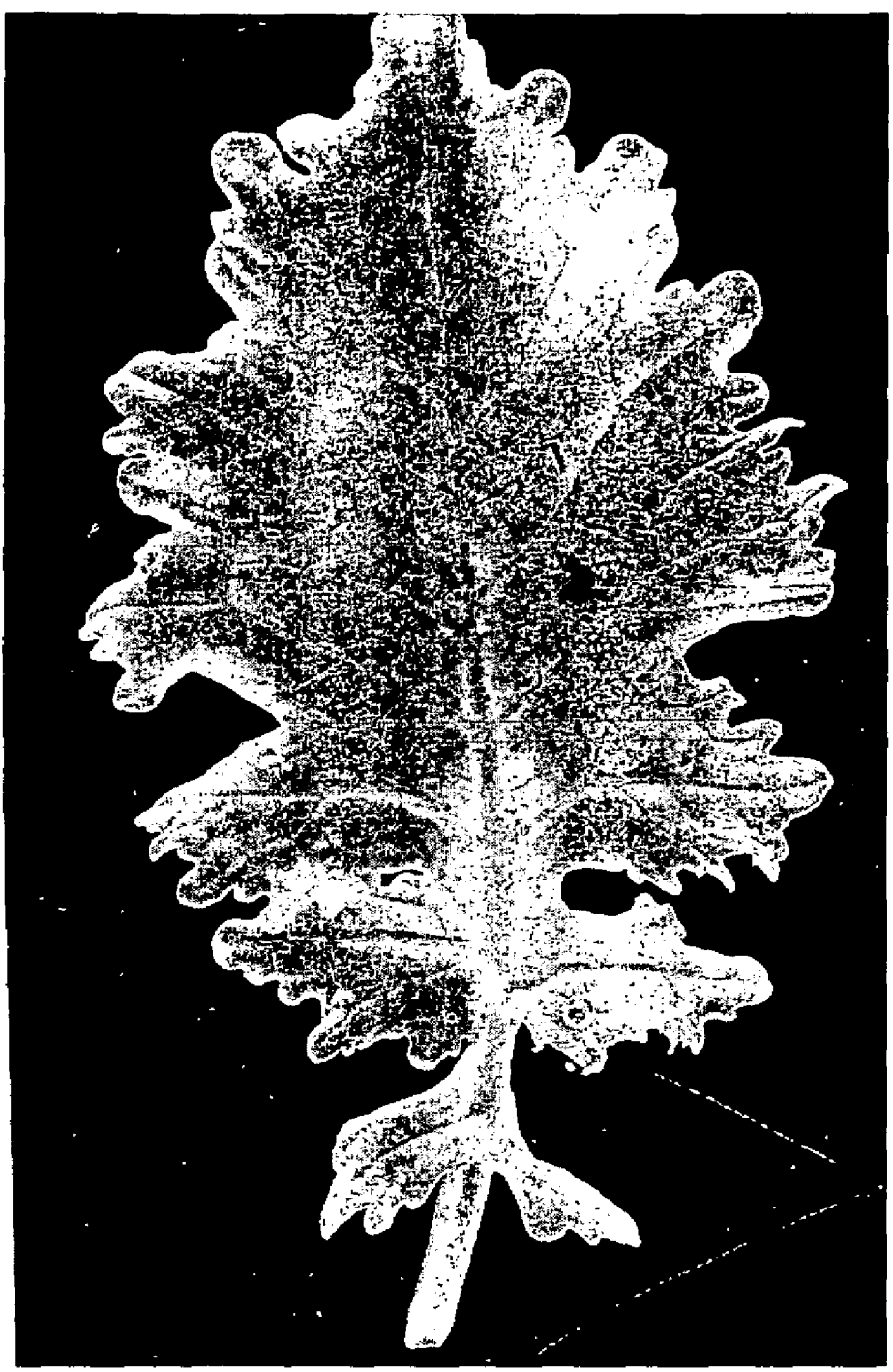
FIG. 10 shows histochemical verification of the local promoter activation.

For describing the spatial expression behavior of the promoter leaves of the rape transformate, AG5947-t49 were employed. The leaves were separated from greenhouse plants and laid on wet filter paper in a transparent plastic box. In the center of one of each leaf halves was pippeted 20 µl *Rhizopus* pektinase (10 u/ml) and water as control. The leaves were incubated for 16 hours at 24° C. and subsequently the GUS-activity was histo-chemically verified. For this the leaves were vacuum infiltrated for 15 seconds with GUS-dye solution (2 mM 5-Bromo-4-chloro-3-indoyl-beta-glucuronid, 50 mM sodium phosphate pH 7.0, 0.5% Triton X-100, 2% N,N,-dimethylformamide) and subsequently incubated for 5 hours at 37° C. The blue coloration of the tissue showed the areas in which high GUS-activity was present. The elicited leaf half of the transformed AG5947-t49 showed, as illustrated in FIG. 10, the spatial strongly limited blue coloration, and therewith promoter activity, about the application point of the pektinase. The remaining tissue areas of the enzyme treated leaf half as well as the water inoculated leaf half of the transgenic line showed no visible GUS-activity. These results show that the induction of the promoter is limited to the inoculation point with the elicitor producing system. The promoter is locally induced in the leaves of transgenic rape plants by elicitors.

Infection of Transgenic Plants

The proof of the pathogen inducibility of the promoter in transgenic plants occurred by infection of leaves of the transgenic rape line AG5947-t48 and AG5947-t49 with the agent causing the disease of rape, *Phoma lingam*. Plants of the transgenic lines AG5947-t48 and AG5947-t49 as well as the non-transgenic line Drakkar were obtained from seed under greenhouse conditions. After the plants reached an age of 6 weeks, in each plant respectively 2 leaves of same size were locally wounded with a nail board, in order to provide an entry port for the fungus. By dipping the wounded leaves in a spore suspension of *Phoma lingam* (100,000 spore/ml) the leaves were inoculated. For control purposes leaves of transgenic and non-transgenic plants were wounded and dipped in water. The plants were subsequently incubated for 7 days under a foil tunnel in the greenhouse at 25° C. and with 90-100% humidity. After 7 days the foil tunnel was removed and after 10 days a histochemical test of the promoter activity was carried out as described above. At this point in time the fungus inoculated leaves show a 6-8 mm sized necrotized zone about the wound points while the water treated controls only exhibit a 1-2 mm sized browning reaction about the wound point. The fungus inoculated leaves of the transgenic plants show in the infection points a local blue coloration brought about by the locally limited promoter activity. The fungus infected leaves of the non-transgenic line Drakkar as well as the wounded and water treated leaves of the non-transgenic and the transgenic lines in comparison exhibit no blue coloration and therewith no reporter gene activity.

Activity Increase of the Promoter in Non-Induced and Induced Leaves of Transgenic Plants with Increasing Plant Age For examination of the development-dependent activity of the promoter in transgenic plants the vector pAG5957-trans was transformed using the protocol described for rape in *Nicotianum tabacum* cv. SR1. The produced tobacco transformates are given identification PR1-52, PR1-54 and PR1-56. The transformate PR1-52 is multiplied and placed in a greenhouse. After the plant has achieved a height of approximately 20 cm, the activatability of the sugar beet promoter is analyzed depending upon the plant age. For this, 6 leaves of different ages on the plant were selected. The oldest, lowest leaf is given reference number 1 and the youngest, highest leaf is given the reference number 6. From the leaf half of one of each leaf there is stamped out, with the aid of a 14 mm cork punch, respectively 15 equally sized leaf disks. Respectively 5 leaf disks are incubated in 90 mm sized petri dishes in salicylic acid containing medium (LS-Medium without Sucrose, 5 mM MES pH 7.0, 0.5 mM SA), in PMG-elicitor containing medium (LS-Medium without Sucrose, 5 mM MES pH 7.0, 1 unit elicitor/ml) or in control medium (LS-Medium without Sucrose, 5 mM MES pH 7.0) for 16 hours at 24° C. On the next day, from each treated leaf half again 5 disks were stamped out for control purposes. The activity of the promoter in these disks as well as the disks incubated over night were measured according to Jefferson (1987) by a quantitative determination of the GUS-activity. After 16 days the corresponding test is repeated with the still intact leaf halves of the leaves 1-6. The tobacco plant is in the meantime grown and approximately 50-60 cm high. The comparison of the measured valves shows (see Table 4b), that the promoter activity in the control leaves for 5 of the 6 analyzed leaves in the repeated test after 16 days (t=16 d) is significantly higher than at the initial examination point (t=0 d). The promoter activity increases with increasing age of the transgenic plants. The wounding or as the case may be the elicitation or as the case may be salicylic acid application leads, in the reporter gene plant with high plant age, in all examined leaves to a higher reporter gene activity and therewith promoter activity. The plant age has however no influence on the relative induction of the promoter by wounding, elicitation or salicylic acid application.

Activity of Promoter Deletion Fragment in Transgenic Plants

In order to examine the influence of the promoter deletions on the reporter gene activity the vectors pAG516 and pAG2339 were transformed with the aid of *A. tumefaciens* in tobacco. The transformates produced with use of pAG516 are given the identification PR4-19, PR4-21 and PR4-22, and the transgenic plants produced with the aid of pAG2339 are given the identification PR8-2, PR8-3 and PR8-12. Cloned plants of the transformates PR4-19, PR4-21, PR4-22, PR8-2, PR8-3 and PR8-12 as well as the transformates PR1-52, PR1-54 and PR1-56 are placed in the greenhouse. After the tobacco plants achieve a height of 60 cm 30-40 leaf disks are stamped out of one leaf and analyzed for their reaction with respect to wound susceptibility, wound susceptibility and pektinase or, as the case may be, wound susceptibility and salicylic acid as described (see activity increase of the promoter in non-induced and induced leaves of transgenic plants with increasing plant age). The three lines PR1-52, PR1-54 and PR1-56 transformed with pAG5947-trans show a slight increase in the reporter gene activity after wounding and a significant induction of the promoter activity after elicitation or as the case may be salicylic acid application (Table 4c). The plants transformed with the construct pAG2339 (PR8-2, PR8-3, PR8-12) show no significant change in the reporter gene activity after wounding, elicitation or as the case may be salicylic acid application. The plants PR8-2, PR8-3 and PR8-12 transformed with the construct pAG516 show a small SA-inducibility in front of the background of a in comparison to the PR1-plants very low reporter gene activity.

Development Activity of the Promoter in Non-Infected Sugar Beets

For investigating the activity of the promoter in the various organs of the sugar beet during the plant development, sugar beet seeds are planted in the field. In the course of a middle European vegetation time, respectively 4, 6, 10, 12, 16 and 22 weeks after planting, respectively 5 whole sugar beet plants were harvested. The plants at no time showed appearance of disease. Total-RNA is isolated from the organs "sink" and "source" leaf, petiole, secondary root and main root (beet body) according to Logemann et al., 1987. The activity of the promoter is determined by a RNA-blot analysis. As hybridization sample a part of the coated region adjacent to the promoter is employed. For this a 1800 bp sized genomic DNA-fragment is amplified from the plant genome of genotype 1K0088 by "inverse polymerase chain reaction (IPCR)".

The cloning of the 1800 bp sized hybridization sample by IPCR occurs in accordance with the work of Does et al. (1991). For this first genomic plant DNA is isolated from leaves of the genotype 1K0088 according to Saghai-Maroof et al. (1984). The genomic DNA (100 ng) is cleaved with the restriction endonuclease BglII, extracted with phenol/chloroform and precipitated in ethanol. The DNA is subsequently taken up in ligation buffer (Life Technologies GmbH, Karsruhe) and ligated in a total volume of 15 µl in the presence of 1 u T4 DNA Ligase (Life Technologies GmbH, Karsruhe, Germany) for 4 hours at 16° C. according to the manufacturer's instructions. In order to be able to clone a part of the coated region attached to the 3'-region of the promoter, a PCR was carried out. For this purpose the oligon-nucleotide primer R1 with the sequence GTG GCT GCT ATA CGA AGA AAA TCT (SEQ. ID NO: 22) and the primer R2 with the sequence ACA CTA TTA TCT ACG CCT CTG ACT (SEQ. ID NO: 23) were employed for the PCR. The primer R1 binds from position 5732-5755 of the nucleotide sequence of FIG. 1 and therewith 192 bp removed from the transcription starting point of the promoter. The primer R2 binds from position 5148-5124 of the nucleotide sequence from FIG. 1 and therewith 254 bp behind the single BjlII cleavage point promoter. The PCR conditions with use of 5 µl of the ligation piece, a primer concentration of 0.2 µM, 1.0 u Advantage Klen Taq-Polymerase-Mix (Clontech Laboratories, Heidelberg, Germany) and 25 µl reaction volume in a Multicycler PTC-200 (MJ Research, Watertown, Mass., USA) as follows:

| | | | | |
|---|---|---|---|---|
| 1 | x | step 1: | 4 min | 95° C. |
| 35 | x | step 2: | 30 sec | 95° C. |
| | | step 3: | 30 sec | 57° C. |
| | | step 4: | 4 min | 72° C. |
| 1 | x | step 5: | 5 min | 72° C. |

The use of this PCR condition results with the primer pair R1/R2 in a 1800 bp sized DNA fragment. This DNA fragment can be subcloned in the vector pGEM-T (Promega Corporation, Madison, Wis., USA) according to standard methods (Sambrook et al., 1989) and the cloned fragment can be inserted as hybridization sample.

For the investigation of the development-dependent promoter activity by an RNA-blot there were divided respectively 10 μg total cell RNA per organ and time point in a denatured formaldehyde-agarose gel as described in Sambrook et al. (1989) The electrophroetic separated RNA is transferred by capillary-blot technique (Sambrook et al. 1989) to a Hybond N nylon membrane (Amersham Pharmacia Biotech, Freiburg, Germany). The radioactive marking of 20 ng of the 1800 bp sized DNA-fragment with 50 μCi $^{32}$P-dATP (6000 Ci/mMol, Amersham Pharmacia Biotech, Freiburg, Germany) occurs with the aid of the Prime-It II Radon Kit (Stratagene GmbH, Heidelberg, Germany) according to the manufacturers instructions. The subsequent hybridization of the RNA-filter with the marked probe or sample occurs in 20 ml hybridization buffer (50% formaldehyde, 5×SSC, 5× Dendardts, 1t SDS, 0.1 mg herring sperm DNA, 40 mM sodium phosphate buffer pH 6.8) at 42° C. in a hybridization oven (Biometra GmbH, Goettingen, Germany) according to Sambrook et al. 1989. After the hybridization the nylon membrane is exposed on an x-ray film (Kodak BioMax MS, Kodak AG, Stuttgart, Germany) in the presence of an amplifier layer (Kodak BioMax MS Intensifying Screen, Kodak AG, Stuttgart, Germany) for 6-24 hours at 80° C. The development of the x-ray film is carried out in a x-ray film developer and x-ray film fixer (Tetenal Photowerk GmbH and Co., Norderstedt, Germany).

The RNA-blot shows that the promoter in the field under non-diseased conditions in 4, 6, 10, 12, 16 and 22 week old sugar beets is of varying strength of activity, depending upon the development condition in the individual plant organs (FIG. 11). The RNA-blot was evaluated in a photo imager (Bioimaging Analyzer BAS 1000, Fujiy Japan), in order to quantify the transcript accumulation. The data of the quantification is reproduced in Table 4.

The accumulation of a transcript provable by IPCR-sample and therewith the promoter activity is only weekly evidenced in leaves of 4 week old plants, however increases with increasing age of the plants and achieves a maximum after 22 weeks. This age dependent increase in the expression applies both for "sink" as well as for "source" leaves. Thus the transcript amount in "source" leaves after 22 weeks is the 28 fold multiple in comparison to the transcript amount in 4 week old plants. For the "sink" leaves after 22 weeks a 14-fold increase in transcript amount can be detected in comparison to 4 week old leaves. The transcript amount in the 16 or as the case may be 22 week old leaves is significantly above the amount that can be found in any time point in the other examined organs. In comparison to the leaves, the activity of the promoter in the roots, secondary roots and petioles over the entire vegetation time (4-22 weeks) exhibits no great variation. In the main root the transcript amount at the 4 week time point is as small as in the leaves, increases up to the 6 week point to the 2-fold amount and decreases thereafter continuously until the 16$^{th}$ week, until at the 22$^{nd}$ week when it rises again to the 2.7 fold of the value of the 4 week point. The transcript amount in the secondary roots increases slightly from the 6$^{th}$ through 10$^{th}$ weeks and falls then until the 22$^{nd}$ week below the value of the 4$^{th}$ week. In the petiole the transcript amount remains constant between weeks 4-16, only to significantly drop until week 22. The promoter activity in the petioles up to the 12$^{th}$ week, in comparison to the other organs, is the highest. While the transcript amount in the "sink" leaves continuously, and the "source" leaves strongly beginning with the 12$^{th}$ week, increase with plant age, this age effect is not to be observed in the petioles.

Expression Behavior Under Damage Conditions in Sugar Beets

Activation of the Promoter in Sugar Beet Leaves Correlated With the Damage by the Leaf Stop Agent *Cercospora beticola*

For the infection of sugar beets with the leaf spot agent *C. beticola* sugar beets of the tolerant genotype 1K0088 and the susceptible genotype 3S0057 were utilized under greenhouse conditions. Two weeks prior to the plant inoculation 20 V8-vegetable juice plates (40% albani-vegetable juice) were immunized with four different *C. beticola* isolates and incubated at 25° C. Immediately prior to the inoculation the fungus growing agar is homogenized together with 1.0 l water in a high capacity stirrer (UM5 Universal, Stephan). The concentration of mycel fragments and fungus spores in the homogenate are determined with the aid of a counting chamber. The inoculum density is adjusted to a concentration of 100,000 fragments/ml by dilution with water. The dilute homogenate is sprayed on the 12 week old sugar beets with the aid of a back sprayer (Gloria 176T). For control purposes plants are sprayed with a fungus-free agar homogenate. The plants are incubated after inoculation for 4 days at 25° C. and 95% humidity in a greenhouse. After the 4$^{th}$ day the humidity is reduced to 60-70%. 4, 7 and 9 days after inoculation leaves from the fungus and agar inoculated plants are sampled and deep-frozen in liquid nitrogen. Thereafter the total cell RNA is isolated according to Logeman et al. 1987. The activity of the promoter in the leaves is determined by an RNA-blot analysis. As hybridization probe the 1800 bp sized genometic DNA-fragment cloned by IPCR was employed, which contained a part of the promoter adjacent the coded region. The activation of the promoter is, as shown in FIG. 12, already evident in leaves which 4 days after inoculation are still free of symptoms (−). With the occurrence of damage symptoms (after 7 or as the case may be 9 days) (+ or as the case may be ++) there occurs a drastic accumulation of a specific transcript. Herein, in stronger afflicted leaves, a higher transcript accumulation is to be observed than in less afflicted leaves. The correlation between gene expression and degree of damage applies both for *C. beticola* tolerant (1K0088) as well as *C. beticola* susceptible genotype (3S0057). Tolerant and susceptible genotype differentiate however in the degree of expression of the gene in healthy leaves. While a weak constitutive expression of the gene is to be observed in healthy leaves of the tolerant genotype, a gene expression in the healthy leaves of the susceptible genotype is not evident.

Rapid Activation of the Promoter in Small and Large Beet Leaves in the Early Infection Phase After *C. Beticola* Infection In order to analyze the activation of the promoter in sugar beet leaves during the early infection phase, sugar beets of the genotype 1K0088 were planted from seed in a test field. Respectively one test parcel with 96 plants, which were 12 weeks old, were inoculated with a *C. beticola* agar mixture or as the case may be for control purposes only with an agar mixture. Immediately after inoculation and subsequently in 1 day intervals small leaves (leaf lengths <10 cm) and large leaves (leaf lengths >20 cm) were taken from the fungus inoculated and the only agar inoculated plants, immediately shock frozen in liquid nitrogen and subsequently stored at −80° C. Total cell RNA was isolated as described and an RNA-blot analysis was carried out. The respective RNA-blots were evaluated with a Phosphoimager (Bio-imaging Analyzer BAS 1000, Fujiy Japan), in order to quantify the transcript accumulation. For each time point and for each leaf type the transcript amount, which was determined for control and for the infected plants, was used to calculate an induction factor (Table 6). This induction factor is a value for the activation of the promoter by fungal infection. The activity of the promoter is rapidly induced both in the small as well as in the large leaves. Already in day 1, the first measure point after inoculation a 3.8-fold induction of the promoter was observed in large leaves. In small leaves a 5.2-fold induction was observed beginning at the second day. A light microscopic examination of the leaf surface showed, that the fungus hyphae grow on the leaves only on day 4 after inoculation. This observation suggests the conclusion that already on day 1 or as the case may be day 2 signal substances of the fungus are recognized and lead to early activation of the promoter.

Following the first activation of the promoter in both leaf types, although time shifted, a similar transient activity behavior can be observed. The promoter activity drops strongly on the second day in the large leaves and on the third day in the smaller leaves, only to climb in the large leaves on the third day and in smaller leaves on the fourth day again to the 3.5 or as the case may be 5.3-fold of the control plants. After this renewed rise, the activity falls a second time in the larger leaves on the fourth day and in smaller leaves on the fifth day. Thereafter the promoter activity climbs until the sixth day in the smaller leaves to the 2.5-fold and in larger leaves to the 3.4-fold. On day 7 the promoter activity both for the small as well as for the large leaves in the infected plants is not much higher than in the non-infected plants. With the first occurrence of visible damage symptoms on the eighth day there can be found in the large leaves, which was all that was examined, a strong increase in the promoter activity, which at day 10 achieves the maximum in this investigation with a 26-fold higher activity in the infected plants.

A Comparison of the Promoter Activity of Different Sugar Beet Genotypes After the Development of a C. beticola Infection Three different sugar beet genotypes were infected with C. beticola under field conditions or as the case may be for control purpose were treated with agar, in order to examine the activity of the promoter during the visible establishment of the leaf spot disease. The genotypes are, in addition to the line 1K0088, the donor plant for the promoter, the lines 4T0057 and 9B3734. Large leaves (>20 cm) are harvested and frozen at −80° C. immediately prior to inoculation (0 day) and as the case may be 10, 14, 17 and 21 days after inoculation from each genotype. Total cell RNA was isolated at each time point from the leaf samples and a RNA-blot analysis was carried out. The transcript amount was quantitatively determined with the aid of a Phosphoimager. The relative transcript amount was, as shown in Table 7, higher for the genotype 1K0088 as well as in the control as well also in the infected plants for each time point than in the plants of genotypes 4T0057 and 9B3734.

*Rhizoctonia solani*

For the infection of sugar beets with the root pathogen *Rhizoctonia solani* sugar beets of the genotype 1K0088 were first planted in a test field from seed. The sowing in the field guaranteed the formation of a strong main root, as not normal in the case of growth under greenhouse conditions. After 3 months the plants were carefully excavated, individually transferred to earth filled 10 l plastic buckets and cultivated for 2 further months in a greenhouse.

A fungus infection occurs in 5 month old sugar beets in a phytocell. For this, 5 holes respectively with a diameter of 1 cm were pressed into the earth with 5 cm separation from the beet. The holes were filled with *R. solani* infected barley meal. In the case of the control plants the inoculation holes were only filled with barley meal. The plants were incubated at 25° C., good watering and a 16/8 hour light/dark cycle.

After 14, 20 and 45 days respectively 3 fungus inoculated and 3 control plants were excavated and the beet body was cleaned. While the infected plants were still free of symptom after 14 days, they showed clear subterranean disease symptoms after 20 or as the case may be 45 days. The periphery of the beet body was deeply browned by the penetration of fungus hyphae in diameter of 1 or as the case may be 3 cm depth. The control plants in comparison, at none of the examined time points, showed any disease symptoms. From each beet body a 1 cm thick tissue disk was cut out. The beet disks of the infected and non-infected plants were respectively collected for a mixed sample and total RNA was isolated according to Logemann et al. (1987). Respectively 10 μg total cell RNA were examined by a RNA blot analysis. The subsequent hybridization showed, that in the control plants after 14, 20 and 45 days no transcripts were to be found (FIG. 13). In the case of the infected plants the first transcripts could be shown only after 20 days. The transcript formation after 45 days was more clearly developed. At time point 14 days no transcripts were evident. The time point and the intensity of the transcript formation correlates with the amount of the visible disease symptom, that is, the promoter is specifically induced in the beet roots by *R. solani* infection. A stronger fungal infection leads to a stronger activation of the promoter in the plant.

Activation of the Promoter in Leaves of Sugar Beets by Wounding and Salicylic Acid In order to investigate the reaction of the promoter in sugar beet leaves to abiotic triggers such as wounds or, as the case may be, on the effect of resistance inductors such as salicylic acid, leaf disks (1 cm diameter) were punched out of 12 week old sugar beets with the aid of a cork stamp. Respectively 100 leaf disks were incubated in control medium (LS-Medium without Sucrose, 5 mM MES pH 7.0) or in salicylic acid containing medium (LS-Medium without Sucrose, 5 mM MES pH 7.0, 2.0 mM SA) for 16 hours at 24° C. Total cell RNA was isolated and an RNA-blot analysis was carried out as described above. The intensity of the hybridization as signal on the RNA-blot was quantified with the aid of a Phosphoimager. The promoter activity of the disks in the control set is not constant over the experiment (Table 8). Based on the 0 hour value, the promoter activity in the control set falls slightly after 3 hours, only to then increase over 6 hours and 11 hours until the 24 hour value. After 24 hours the transcript amount in the control set is approximately 3-fold higher than in the beginning of the experiment (0 h). This rise in the promoter activity is to be traced back to the wounding of the leaf tissue during the stamping out of the leaf disks. The promoter thus shows a wound-inducibility in the leaves. In the salicylic acid containing medium there is likewise a rise in the transcript amount depending upon the time (Table 8). However other than time point 0 h the transcript amount is significantly higher in all test points than in the control set. Thus the transcript amount after 24 hours is approximately the 8.5-fold of the 0 h value. The cause of the higher activity of the promoter in the salicylic acid containing medium is the inducibility of the promoter by salicylic acid.

TABLE 1

Overview over the Promoter Derivatives Produced by the PCR-Techniques

| Identification and Binding Position of the Primer in the Promoter Sequence of FIG. 1 | Identification and Size of the PCR-Product (in parenthesis) | Plasmid Identification and Sequence Region of the Promoter Derivative After Subcloning the Adjacent PCR-Products | |
|---|---|---|---|
| P0 | (1-7) | | |
| P4480 | (4484-4459) | P0/P4480 (4503 bp) | pA4480, 1-4480 |
| P4047 | (4054-4027) | P0/P4047 (4073 bp) | pA4047, 1-4047 |
| P3017 | (3028-2999) | P0/P3017 (3047 bp) | pA3017, 1-3017 |
| P2661 | (2666-2637) | P0/P2661 (2685 bp) | pA2661, 1-2661 |
| P2339 | (2347-2319) | P0/P2339 (2366 bp) | pA2339, 1-2339 |
| P1889 (1913 bp) | (1894-1869) | P0/P1889 | pA1889, 1-1889 |
| P1777 | (1781-1755) | P0/P1777 (1800 bp) | pA1777, 1-1777 |
| P1777* | (1781-1755) | P0/P1777* (1800 bp) | pA1777*, 1-1777 |
| P814 | (824-799) | P0/P814 (843 bp) | pA814, 1-814 |
| P368 | (378-349) | P0/P368 (397 bp) | pA368, 1-368 |

[1]PCR-Fragments were cleaved with the restriction endonucleases Sa/I and SmaI and cloned in the Sa/I and SmaI treated vector pBluescriptII KS+.

TABLE 2

Elicitor Inducibility of the Sugar Beet Promoter in Transgenic Rape Plants Leaves of transgenic (transformation vector AG5947-t) and non-transgenic greenhouse plants were incubated in the presence (induction medium) or absent (control medium) of an elicitor freeing enzyme for 16 hours. The activity of the promoter was measured by a quantitative determination of the β-Glucuronidase activity.

| Genotype | Control Medium Specific GUS-Activity (pMol Mu × $min^{-1} \times mg^{-1}$) | Induction Medium Specific GUS-Activity (pMol Mu × $min^{-1} \times mg^{-1}$) | Induction Factor |
|---|---|---|---|
| Non-transgenic line Drakkar | 6.68 | 6.61 | 1.0 |

TABLE 2-continued

Elicitor Inducibility of the Sugar Beet Promoter in Transgenic Rape Plants Leaves of transgenic (transformation vector AG5947-t) and non-transgenic greenhouse plants were incubated in the presence (induction medium) or absent (control medium) of an elicitor freeing enzyme for 16 hours. The activity of the promoter was measured by a quantitative determination of the β-Glucuronidase activity.

| Genotype | Control Medium Specific GUS-Activity (pMol Mu × $min^{-1} \times mg^{-1}$) | Induction Medium Specific GUS-Activity (pMol Mu × $min^{-1} \times mg^{-1}$) | Induction Factor |
|---|---|---|---|
| AG5947-t48 | 14.0 | 247.6 | 17.7 |
| AG5947-t49 | 138.7 | 1507.9 | 16.9 |

TABLE 3

Activation of the Promoter in Leaves, Shoots and Roots of the Transgenic Rape Line AG5947-t49 after Wounding and Elicition by Pektinase.

| | Specific GUS-Activity[1] | Separated Specific GUS-Activity[1] | Separated + Elicitor Specific GUS-Activity[1] | Wound-Induction[2] | Elicitor-Induction[3] |
|---|---|---|---|---|---|
| Leaf | 14.3 | 75.5 | 5404.0 | 5.3 | 72.0 |
| Shoot | 158.0 | 1315.4 | 4546.3 | 8.3 | 3.5 |
| Root | 72.0 | 520.0 | 4714 | 7.2 | 9.0 |

[1]Specific gus-Activity: pMol Mu × $min^{-1} \times mg^{-1}$
[2]Relationship of the specific GUS-Activity of the separated leaves to the specific activity of the control leaves.
[3]Relationship of the specific GUS-Activity of the separated leaves to the specific activity of the separated and elicited leaves.

TABLE 4

Induction of the Sugar Beet Promoter in Leaves of Transgenic Rape Plants by Salicylic Acid and PMG-Elicitor

| | AG5947-t38 Specific GUS-Activities[1] | Induction | AG5947-t48 Specific GUS-Activity[1] | Induction |
|---|---|---|---|---|
| Control | 24.47 | | 1.86 | |
| SA (0.5 mM) | 485.3 | 19.8 | 17.2 | 9.2 |
| PMG-Elicitor (25 µg/ml) | 187.0 | 7.7 | 9.3 | 5.0 |

[1]Specific GUS-Activity: pMol Mu × $min^{-1} \times mg^{-1}$

TABLE 4b

Rise of the Promoter Activity in Leaves of a Transgenic PR1-52 Tobacco Plant With Increasing Plant Age.

| | Control Specific GUS-Activity* | Separated Specific GUS-Activity* | Separated + Elicitor Specific GUS-Activity* | Separated + SA Specific GUS-Activity* | Wound-Induction[1] | Elicitor-Induction[2] | SA-Induction[3] |
|---|---|---|---|---|---|---|---|
| Leaf 1 | | | | | | | |
| t = 0 d | 59.46 | 238.00 | 327.9 | 314.92 | 4.0 | 5.5 | 5.3 |
| t = 16 d | 28.25 | 325.17 | 394.28 | 861.82 | 11.5 | 14.0 | 30.5 |
| Leaf 2 | | | | | | | |
| t = 0 d | 14.98 | 116.37 | 130.17 | 205.53 | 7.8 | 8.7 | 13.6 |
| t = 16 d | 76.75 | 160.12 | 1166.49 | 2358.18 | 2.1 | 15.2 | 30.7 |

TABLE 4b-continued

Rise of the Promoter Activity in Leaves of a Transgenic PR1-52 Tobacco Plant With Increasing Plant Age.

| | Control Specific GUS-Activity* | Separated Specific GUS-Activity* | Separated + Elicitor Specific GUS-Activity* | Separated + SA Specific GUS-Activity* | Wound-Induction[1] | Elicitor-Induction[2] | SA-Induction[3] |
|---|---|---|---|---|---|---|---|
| Leaf 3 | | | | | | | |
| t = 0 d | 10.38 | 83.31 | 270.19 | 225.07 | 8.0 | 26.0 | 21.7 |
| t = 16 d | 63.38 | 204.38 | 863.05 | 555.62 | 3.2 | 13.6 | 8.8 |
| Leaf 4 | | | | | | | |
| t = 0 d | 4.59 | 48.87 | 172.53 | 117.97 | 10.6 | 37.6 | 25.7 |
| t = 16 d | 35.06 | 141.6 | 482.88 | 1561.3 | 4.0 | 13.8 | 44.5 |
| Leaf 5 | | | | | | | |
| t = 0 d | 4.78 | 58.24 | 185.6 | 140.37 | 12.2 | 38.8 | 29.4 |
| t = 16 d | 134.96 | 426.23 | 512.63 | 1220.71 | 3.2 | 3.8 | 9.0 |
| Leaf 6 | | | | | | | |
| t = 0 d | 0.33 | 37.11 | 121.41 | 106.35 | 111.5 | 364.6 | 319.4 |
| t = 16 d | 21.33 | 146.74 | 1069.58 | 1003.47 | 6.9 | 50.1 | 47.0 |

*Specific gus-Activity: pMol Mu × min$^{-1}$ × mg$^{-1}$
[1]Relationship of the specific GUS-Activity of the separated leaves to the specific GUS-activity of the fresh harvested controlled leaves.
[2]Relationship of the specific GUS-Activity of the fresh harvested controlled leaves to the specific GUS-activity of the separated and elicited leaves.
[3]Relationship of the specific GUS-Activity of the fresh harvested control leaves to the specific GUS-activity of the separated and salicylic acid treated leaves.

TABLE 4c

Promoter Activity of the Deletion Construct pAG 516 and pAG2339 as well as the Translational Fusion pAG5947-trans in Leaves of Transgenic Tobacco Plants.
The Plants PR1-52, PR1-54 and PR1-56 were transformed with the Construct pAG5947-trans. Further the plants PR4-19, PR4-21 and PR4-22 were transformed with pAG516 and the plants PR8-2, PR8-3 and PR8-12 were transformed with the Construct pAG2339. SR1 is the non-transgenic starting line.

| | Control Specific GUS-Activity* | Separated Specific GUS-Activity* | Separated + Elicitor Specific GUS-Activity* | Separated + SA Specific GUS Activity* | Wound-Induction[1] | Elicitor-Induction[2] | SA-Induction[3] |
|---|---|---|---|---|---|---|---|
| PR1-52 | 15.1 | 35.96 | 199.21 | 218.93 | 2.4 | 13.2 | 14.5 |
| PR1-54 | 20.87 | 43.29 | 216.38 | 167.83 | 2.1 | 10.4 | 8.0 |
| PR1-56 | 80.07 | 475.82 | 938.61 | 661.19 | 5.9 | 11.7 | 8.3 |
| PR4-19 | 7.4 | 2.9 | 4.0 | 16.6 | 0.4 | 0.5 | 2.3 |
| PR4-21 | 36.6 | 38.8 | 23.7 | 21.3 | 1.1 | 0.7 | 0.6 |
| PR4-22 | 5.4 | 2.7 | 4.0 | 19.3 | 0.5 | 0.8 | 3.6 |
| PR8-2 | 8.4 | 0 | 0 | 1.7 | 0 | 0 | 0.2 |
| PR8-3 | 26.9 | 31.0 | 0 | 0 | 1.2 | 0 | 0 |
| PR8-12 | 0 | 5.3 | 0 | 0 | 0 | 0 | 0 |
| SR1 | 7.9 | 0 | 2.8 | 6.2 | 0 | 0.4 | 0.8 |

*Specific gus-Activity: pMol Mu × min$^{-1}$ × mg$^{-1}$
[1]Relationship of the specific GUS-Activity of the separated leaves to the specific GUS-activity of the fresh harvested controlled leaves.
[2]Relationship of the specific GUS-Activity of the fresh harvested controlled leaves to the specific GUS-activity of the separated and elicited leaves.
[3]Relationship of the specific GUS-Activity of the fresh harvested control leaves to the specific GUS-activity of the separated and salicylic acid treated leaves.

TABLE 5

Comparison of the Developmental Dependent Activity of the Promoter
in 5 Different Organs of the Sugar Beet
Total Cell-RNA was isolated after planting at various developmental
stages (4, 6, 10 12, 16, 22 weeks) from "sink"- and "source"-leaves,
from Petioles, main roots and secondary roots of sugar beets and examined
using a RNA-Blot analysis. As hybridization probe a 1800 bp sized DNA-
fragment obtained by IPCR was employed. The transcript amount formed
by the promoter activity was quantified with the aid of a phosphoimager
and represented in the table for each test time point.

|  | 4 Week | 6 Week | 10 Week | 12 Week | 16 Week | 22 Week |
|---|---|---|---|---|---|---|
| "Source" leaf | 43[1] | 98 | 109 | 86 | 774 | 1191 |
| "Sink" leaf | 36[2] | 44 | 74 | 136 | 356 | 502 |
| Petiole | n.b.[3] | 162 | 195 | 198 | 201 | 61 |
| Main Root | 49 | 100 | 78 | 38 | 42 | 132 |
| Seconary Root | n.b.[3] | 83 | 140 | 62 | 74 | 46 |

[1]As "source" leaf the first leaf pair was selected in 4 week old sugar beets.
[2]As "sink" leaf in 4 week old sugar beets the Keim (?) leaves were selected.
[3]n.b. = not determined.

TABLE 6

Induction of the Sugar Beet Promoter in small and
large Sugar Beet Leaves After Infection by Cercospora beticola
Total cell-RNA from fungus inoculated and control plants
were examined using RNA-blot analysis. The transcript amount
produced by the promoter activity was quantified with the aid of a
phosphoimager. The quotient of the transcript amount of the
control plants and the transcript amount of the inoculated plants
was used as induction factor (1 = no induction, 2 = double
transcript amount, etc.).

| Time After Inoculation (Days) | Small Leaves (<10 cm) Induction Factor | Large Leaves (>20 cm) Induction Factor |
|---|---|---|
| 0 | 1.1 | 1.5 |
| 1 | 1.0 | 3.8 |
| 2 | 5.2 | 1.4 |
| 3 | 1.1 | 3.5 |
| 4 | 5.3 | 1.6 |
| 5 | 1.6 | 2.0 |
| 6 | 2.2 | 3.4 |
| 7 | 1.1 | 1.1 |
| 8 |  | 1.9 |
| 9 |  | 2.9 |
| 10 |  | 26.0 |

TABLE 7

Comparison of the Activity of Different Alleles of the Promoter
in Three Different Sugar Beet Genotypes after Infection by
Cercospora beticola
Total cell-RNA from fungus inoculated and control plants was
examined by RNA-Blot analysis. The transcript amount formed by
the promoter activity was quantified with the aid of a
phosphoimager and indicated in the table for each test day. The
results of the control plants are indicated with (−) and the results
of the fungus inoculated plants are indicated with (+). n.b. = not
determined.

| Genotype | 0 Day | 10 Day | 14 Day | 17 Day | 21 Day |
|---|---|---|---|---|---|
| 4T0057 (−) | 323[1] | 332 | 225 | 254 | 633 |
| 4T0057 (+) | n.b. | 756 | 790 | 1920 | 3444 |
| 9B3734 (−) | 265 | 277 | 432 | 576 | 477 |
| 9B3734 (+) | n.b. | 781 | 6303 | 7653 | 10685 |
| 1K0088 (−) | 1753 | n.b. | 787 | 4492 | 2762 |
| 1K0088 (+) | n.b. | n.b. | 10152 | 8537 | 22598 |

[1]Measured values are given in PSL (photo stimulated luminescence)-units.

TABLE 8

Activation of the Promoter in Leaves of Sugar Beets by Wounding
and Salicylic Acid Leaf disks from sugar beets were incubated
according to the indicated time duration in liquid medium in the
presence and absence of 2.4 mM salicylic acid. RNA was isolated
from the disks and RNA-Blot analysis was carried out. The
transcript amount formed by the promoter activity was quantified
with the aid of a Pphosphoimager and represented in the table for
each test time point.

| Time (h) | Control | Control + 2.0 mM Salicylic Acid |
|---|---|---|
| 0 | 107[1] | 81 |
| 3 | 61 | 107 |
| 6 | 214 | 284 |
| 11 | 211 | 513 |
| 24 | 339 | 688 |

[1]Measured values are given in PSL (photo stimulated luminescence)-units.

LITERATURE

Altschul, S. F. et al. (1990). Basic Local Alignment search tool, J. Mol. Biol. 215: 403-410

An, G. (1987). Binary Ti vectors für plant transformation and promoter analysis. Methods Enzymol. 153, 292-305.

DE 4207358 A1 (Institut für Genbiologische Forschung Berlin GmbH). Expressionskassette und Plasmide zur schliesszellenspezifischen Expression und ihre Verwendung zur Herstellung transgener Pflanzenzellen und Pflanzen.

da Costa e Silva, O., Klein, L., Schmelzer, E., Trezzini, G. F., and Hahlbrock, K. (1993). BPF-1, a pathogen-induced DNA-binding protein involved in the plant defense response. Plant Journal 4 (1), 125-135.

De Greve, H., Dhaese, P., Seurinck, J., Lemmers, M., Van Montagu, M., and Schell, J. (1982). Nucleotide sequence and transcript map of the *Agrobacterium tumefaciens* Ti plasmid-encoded Octopine synthase gene. J. Mol. Appl. Genet. 1 (6), 499-511.

Depicker, A., Stachel, S., Dhaese, P. Zambryski, P., and Goodman, H. M. (1982). Nopaline synthase: Transcript mapping and DNA sequence. J. Mol. Appl. Genet. 1 (6), 561-573.

Does, M. P., Dekker, B. M. M., de Groot, M. J. A., and Offring a, R. (1991). A quick method to estimate the T-DNA copy number in transgenic plants at an early stage after transformation, using inverse PCR. Plant Mol. Biol. 17, 151-153.

Dzelzkàlns, V. A., Thorsness, M. K., Dwyer, K. G., Baxter, J. S., Balent, M. A., Nasrallah, M. E., and Nasrallah, J. B.

(1993). Distinct cis-acting elements direct pistil-specific and pollen-specific activity of the *Brassica* S locus glycoprotein gene promoter. Plant Cell 5, 855-863.

EP 0344029 B1. (Plant Genetic Systems, N.V. 1040 Brussel). Plants with modified stamen cells.

Fennell von, et al., Plant Cell Rep. 11 (1992), 567-570

Gottschalk, T. E., and Mikkelsen, J. D. (1998). Immunolocalization and characterization of a beta-1,3-glucanase from sugar beet, deduction of ist primary structure and nucleotide sequence by cDNA and genomic cloning. Plant Science 132, 153-167.

Greiner, S., Krausgrill, S., and Rausch, T. (1998). Cloning of a tobacco invertase inhibitor. Plant Physiol. 116, 733-742.

Höfgen R. & Hesse H.: DE 19607697, erteilt Sep. 4, 1998/ WO 97/32027,veröff. Apr. 9, 1997

Horsch, R. B., Fry, J. E., Hoffmann, N. L., Rogers, S. G., Fraley, R. T. (1985). A simple and general method for transferring genes into plants. Science 227, 1229-1231.

Jähne et at., Theor. Appl. Genet. 89 (1994), 525-533)

Jefferson, R. A. (1987). Assaying chimeric genes in plants: The GUS gene fusion system. Plant Mol. Biol. Rep. 5, 387-405.

Linsmaier, E. M., and Skoog, F. (1965). Organic growth factor requirements of tobacco tissue cultures. Plant Physiol. 18, 100-127.

Logemann, J., Schell, J., and Willmitzer, L. (1987). Improved method for the isolation of RNA from plant tissue. Anal. Biochem. 163, 16-20.

Lois, R., Dietrich, A., Hahlbrock, K., and Schulz, W. (1989). A phenylalanine ammonia-lyase gene from parsley: Structure, regulation and identification of elicitor and light-responsive cis-acting elements. EMBO J. 8, 1641-1648.

Odell, J. T. Nagy, F., and Chua, N.-H. (1985). Identification of DNA sequences required for activity of the cauliflower mosaic virus 35S promoter. Nature 313, 810-812.

Ohl, S., Hedrick, S. A., Chory, J., and Lamb, C. J. (1990). Functional properties of a phenylalanine ammonia-lyase promoter from *Arabidopsis*. Plant Cell 2, 837-848.

Ohme-Takagi, M., and Shinshi, H. (1995). Ethylene-inducible DNA-binding proteins that interact with an ethylene-responsive element. Plant Cell 7, 173-182.

Raventó, D., Jensen, A. B., Rask, M.-B., Casacuberta, J. M., Mundy, J., and San Segundo, B. (1995). A 20 bp cis-acting element is both necessary and sufficient to mediate elicitor response of a maize PRms gene. Plant J. 7(1), 147-155.

Rushton, P. J., Torres, J. T., Parniske, M., Wernert, P., Hahlbrock, K., and Somssich, I. (1996). Interaction of elicitor-induced DNA binding proteins with elicitor response elements in the promoters of parsley PR1 genes. EMBO J. 15, 5690-5700.

Rushton, P. J., and Somssich, I. E. (1998). Transcriptional control of plant genes to pathogens. Curr. Opion. In Plant Biol. 1, 311-315.

Saghai-Maroof, M. A., Solimanm, K. M., Jorgensen, R. A., ans Allard, R. W. (1984). Ribosomal DNA spacer length polymorphism in barley: mendelian inheritance, chromosomal location and population dynamics. Proc. Natl. Acad. Sci. USA 81, 8014-8018.

Sambrook, J., Fritsch, E. F., and Maniatis, T (1989). In Molecular Cloning, A Laboratrory Manual. (Cold Spring Harbor Laboratory Press, New York).

Shah, J., and Klessig, D. F. (1996). Identification of a salicylic acid-responsive element in the promoter of the tobacco pathogenesis-related rn-1,3-glucanase gene, PR-2d. Plant J. 10, 1089-1101.

Stoeger et al. Plant Cell Rep. 14 (1995), 273-278

US 005608150A (Monsanto Company). Fruit specific promoters.

Valent, B. (1978). Dissertation, University of Colorado, Seite 8.

Velten, J., Velten, L., Hain, R., and Schell, J. (1984). Isolation of a dual promoter fragment from Ti plasmid of *Agrobacterium tumefaciens*. EMBO J. 12, 2723-2730.

WO 92/17591 (Danisco A/S) A Plant Chitinase gene and use thereof.

WO 94/02619 (Pioneer Hi-Breed International, Inc.) A brassicae regulatory sequence for root-specific or root abundant gene expression.

Wo 97/28268 (The Minister of Agriculture and Agri-Food Canada). Promoter from tobacco.

Wo 97/27307 (Agritope, Inc). Raspberry promoters for expression of transgenes in plants.

WO 97/32027 (Max-Planck-Gesellschaft zur Forderung der Wissenschaften). Sugarbeet storage-root-tissue-specific regulon.

WO 98/18940 (BASF Aktiengesellschaft). Leaf-specific gene sa expression in transgenic plants.

WO/98/45460 (Rhone-Poulenc Agro). A sunflower albumin 5'regulatory region for the modification of plant seed lipid composition.

SEQUENCE LISTING

```
<160> NUMBER OF SEQ ID NOS: 25

<210> SEQ ID NO 1
<211> LENGTH: 5947
<212> TYPE: DNA
<213> ORGANISM: Beta vulgaris
<220> FEATURE:
<221> NAME/KEY: CAAT_signal
<222> LOCATION: (42)..(45)
<220> FEATURE:
<221> NAME/KEY: TATA_signal
<222> LOCATION: (33)..(36)
<220> FEATURE:
<221> NAME/KEY: promoter
<222> LOCATION: (1)..(5947)
<300> PUBLICATION INFORMATION:

<400> SEQUENCE: 1
```

```
tttattgaat catcatagat attaccagtt tttataggat aattgagttg aaaagtctac      60
actatagttc aaaattttga tacaagaata ataaagaaaa tacgaatatg accaacacta     120
gggtcgtttt gtgataaaat ttcaaacaaa aaacgtcgtt tatggacata attcaatgct     180
aattatgact gaagattttc ttcgtatagc agccacttaa cttgtgtttt gggctaattt     240
tttctttact tgtgagtgag tacgttaaat gtggaaagtt ggaagattga gatcattaca     300
aagactagat aattgatgaa tgcctaattt aatctagtat tgtagtcagg aaggactaac     360
acgtcaaaat gaattatatt aattccttgc tatatggtgt aatagtcttt tacttcgtat     420
tgcatcatat gattttaaga gaatgatgca tatcatggta ctaacgcgta tcgtttgtag     480
gatctcattt acttgtcaaa ctctcttcat ctctagatat tccttttagc ttttgaggtt     540
taattttgcc catacatcat tcttaaacca tatacataca ggtcctcttg aaaattttgg     600
ggttccgatt ctaatatgaa aattggctcc ctaaatttat agaaaataaa aatggaaggt     660
tagagttcta aagaaggaaa gttgaaaatc taaagataga ttattgacaa atttattaag     720
ggtgggaaac cagggtgatt tcttcggtaa aattttcaaa ataatatatt ttgggggtca     780
tgtgctgttt ggctccttgc acactattat ctacgcctct gactatataa gtaaatgtta     840
taatgttatt ttgcaatata ttaataaaaa aggagtaaat tgagtggtta gagttatcac     900
gcaaaaaaaa aaaaaaggat tgtaaaacaa tgttcactgt gttatgtact atgtttcaac     960
tatattagat attttgagat tatgttgaaa catgattcat acatacaaaa aataaaacaa    1020
tgaaataaag ttaaacaaga aacaaagatt tttaacgtgg ttcaatctac tcgagatcta    1080
tatctaccaa attcactaat agtggactcc cctaatggtg ttgccaagtt gaatcaaagt    1140
acaaattctt gtacctaata aatactctct ataatagtaa aattacataa atatctcctt    1200
aatatacgct tctcaatcaa ttactccctc cgtcttttt tatttgctac attttaccat    1260
ttaggggtgt ttcaatttat ttgctacatt tgcaaatatt tccatatata gtacatatgt    1320
cccacacttt atttacaaat ttgccatcac tcccttcttg attttgtaaa tgtttccata    1380
tataatacat aggtcccaca atttacctat ttgcttttt gttaattcca tttatgtcaa    1440
tggtccccac tccctccttg gtctttgtga aaaagtgctt gtagcaaata aaaaaagacg    1500
gagggagtag aacattatca aacctttttat aaagtaaatt atctttgcac aaactagata    1560
ataacttcta caaaaaaaag gtactccctc tattttaaaa tataaggcat ttatattta    1620
cgagaatttg ctttgactac aaatatctct caaatgtgat aaataaaaat cataaatatt    1680
ataccgttgg attcgtcttg aaaaatacta taataatatt atttttcata attttctatc    1740
aacataaatt aagagtaatt aacggtcaaa gttcgacctc gaacatcgtg cgtgccttat    1800
attgtgaaac ggagggagta ttattttaga ttcaaatatt taacaaagat actattttgt    1860
ttaattaaga ttattttcca tagaacaaca tattttgaa aatcttttc attatgtgaa     1920
attactacca ttagtctatt tatactaact tcaatacgtc ttggggccgg ccataactat    1980
agttattatt catactacta acactactag atataaatag cttaattaat tatgttattg    2040
ataataattt taccaataac acttaggtct tagggcaata gtaaccaagt tagttacttc    2100
tacaatttac taaagaaaa atctaactac tcttcaatct tcaatctttc aaacttgagc    2160
tccaataaaa cttttttaaag taatcaataa taatctgcat catatatacg aacatacata    2220
tatgatatat agatgcaagg atagtttatg ctatcatcaa aaaattcaaa actcttaagg    2280
tcataataac atatataaca attttatatt attgttccgg ttgcaaaaca gtggacgacc    2340
ttcaataagg ccgccaagga ttgagtgcgc gtccgctagt gaataactgc aaggaaacaa    2400
```

-continued

```
acgtaaacta tcctaggggg atgcaaggaa accccctcca acgctcaagt tagtattatg    2460
tccggaaagg tttagagaga gaaagtagag agagaagaaa attagtgtac gagcagaata    2520
gtaatactgg gcttttcata aaagtattat tcatttgaca gactgcataa tcctcataca    2580
cgtgtatggt tgtgatttgc ctcaataaga aacgattcct cttttttgtc ttattagatg    2640
actgccaaat tgtcagacaa cttcactaaa ttaatctcag gcgttgctat ggatatgctt    2700
catgatcgcg tcctcgtaca atcctcgcgg acatattgat gtgtccgcta gcatacttgg    2760
gttataccca tacaattatt ataattagaa atttgcggtc ataaaatcga tctcaaaagt    2820
gaaaaatgac aaaaaaaaaa aaaattagaa caatattatg tggcgtgccg cctgtgaata    2880
attcttgaat cctccaattt agaaaagtct acaaaattgt cttatttagt actattgtac    2940
tcgcgacgca actaactatt agtcaggaac gaaagtattt aatttcacaa gtcgttttaa    3000
tatgttctcc tcttgacttc ttgttatact agccttcata tgcacgcgat gcgtgcgtta    3060
atttcaaaat ttgttattct attagatact ccattcgtac tttatttatg attaaactta    3120
aatgtgaaaa attcaacagt tagatgaatt tagatatatt aattcactaa tgtaaaaaaa    3180
taaaaagttt gtgaatgatt gttaacatta attttttgtg aatgaatttt gaacaaaaag    3240
aacaaaaata atgagtttgt ttaactgaat taaagagtat caaaggtagt gaatgttcag    3300
acttttcatg tgcacgttat gtatgccatc ttttttttat aaggtataaa tattttgtcc    3360
atttaatttt tgattgaagt atttgatgca tatatcattt taaacttgtt ttaaatggca    3420
agttggaatg agaattttta aatgatttgc ttttgtaatt tttttcattc tattaattag    3480
atcattaagg gtattttagg cacttcaaaa gaggacacca cacctccttc cttggcttat    3540
ataataaaga tgagtgacga cgactataac ttatggagtc ctccctcggt tgagtggttg    3600
ttacttgtta ggtcttacag cattttgatc acttcttatc tattactaga aattagaata    3660
aagaattcct ccgttgtctc ttagttatta tcacatactt ccacttgcac cgttgtaatt    3720
gttaggtgta aaatattgac ttttggtcat ttaaataatt tttgtaatat ttgacataaa    3780
aaattctaat ttctagatca ttttagtttt tgattatttt gcaatagttc ttaggtgggg    3840
aagggcctta ctcaaaaaca aattgaagtg tgttaaatcg gctatatacc atgaacccac    3900
attagattaa tatatatgga cataaattca aagttatata tactttcaca taaaagagaa    3960
aaatatttca cttaaaagaa atggaggaag tatattacta tttgagtagg ttcgtgcaaa    4020
agttaggaat tttattttat tatctaaaat tggaattatt ttggaaaaat ggttgaaagt    4080
ggagattttt ttttttttgaa agtaagatta ttaattttta tattatattt ttgaaaaatt    4140
tactttagct ccctccccca accaaaaaaa atacaaagtc aattagagaa agtacatcct    4200
atttatgttt aagactagag ctgattagag tgagactggc tccatttgaa aaatgcctgg    4260
gcttaaacaa attttttggt cccggtccga cccgatattc ttttttgagtt ttgggcaacc    4320 taaaacacat ttttttgttc aaattttgac ttgatcggat tttgacctga aagctcgac    4380 attttttgccc taagaaagcg gggtttgggc acaaaaagcg tgttgaaatt tggcccagcc    4440
cgactaatgg tcaattttttt tggggaggcc cggcatgaac ccggttggct cacctttga    4500 tcactaagac aatgacatct tgttacgagc atgtgagcct atgagagagc catacccgat    4560
acatgcgttg atatatagaa aatataattg gtagaaaaaa taactttaaa attttatttc    4620
atcattaaga agacaatgac attttgtttt aataatttgc aaattgatta catacgggtc    4680
ttttaggcat cgtaatagag atatgattga gccattgagg gaaggtttgc acatatgtga    4740
```

```
tatgtgcaat ataattacta ctccctccgt cccaatttag ttgctacatt ttgatcgtag      4800
gcactattca cgtcataact ttgactatat tttacttcat atatatatat aagaaaaaac      4860
atagtcatgc atgttggatc ttctttgatt cgtcccaatt tgtattttc aaatatataa      4920 tttttattat atatgtaact caaaatattg gtgttgcatc tcgtaaactg tgataaaaca      4980
aatgtagcaa ctaaattggg acagagggag taattagtaa ccttgtaccc ctggaaaaag      5040
aaaatagcat cctttagcc tgtagctccc ttgtcgccac tattaattga cgttcaatta      5100
gctagggtct gatgatacac atactaatcc ttcatttcta aattccaagc atacttcatt      5160
ctcaataagt taacaaaatg cgcattctct tattaattag gtagtacaaa gtacaaatac      5220
acgtttgata tgaaaagtta cgatttgcat attgcaaaca atatctagaa attccatact      5280
tttggctagc taattgtaag cctaatcagt taaagtttaa tgaaccatac ttaggctgct      5340
gatcaggagt aaaaatccca aaattatgct catcttcatc ccctggtttc ttatcttcat      5400
caaacatggc aaacaagaaa gtctcaattg ctctccctgg tttcaatgga gtcccattct      5460
tcacatggtt gatcaaattg gtgacatact tctttgcatt atcgtgatta gccccgaaac      5520
caccgcctga cgcccacccg gtctcggacg taagcaatga aacgtcgggc gcaccaacct      5580
tatctaaagc cgcatatgtt gcatcggcaa gtgcatcaaa taaattttgg taatttctgc      5640
cattattatc gtccgtaaca acagttccag gagaagtaaa taaagcgtaa tcaagagaaa      5700
tttgttttga attacgttgg taagcaaagt aagggtatat taaccatgaa aggtgaacca      5760
ttttgtttta taaagttgat tattggtgta atatattgaa cgttaccaaa ttgtccatta      5820
gatggtggga aggcgttttc gactaggctt gtaccaacgg atgtagaaac cttaatttga      5880
tcacctaaat tgttagaatt aagtgcattg agaatatttt gcatggctgg tagaactgat      5940
gaagctt                                                               5947

<210> SEQ ID NO 2
<211> LENGTH: 12
<212> TYPE: DNA
<213> ORGANISM: Petroselinum crispum

<400> SEQUENCE: 2
wctmacctam cm                                                           12

<210> SEQ ID NO 3
<211> LENGTH: 11
<212> TYPE: DNA
<213> ORGANISM: Nicotiana tabacum

<400> SEQUENCE: 3
taagagccgc c                                                            11

<210> SEQ ID NO 4
<211> LENGTH: 10
<212> TYPE: DNA
<213> ORGANISM: Nicotiana tabacum

<400> SEQUENCE: 4
ttcgacctcc                                                              10

<210> SEQ ID NO 5
<211> LENGTH: 10
<212> TYPE: DNA
<213> ORGANISM: Beta vulgaris

<400> SEQUENCE: 5
```

-continued

```
ttcgacctcc                                                          10

<210> SEQ ID NO 6
<211> LENGTH: 10
<212> TYPE: DNA
<213> ORGANISM: Beta vulgaris

<400> SEQUENCE: 6
ttcgacctcg                                                          10

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
actgaccacc cggggtggat ttattg                                        26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccgggtcgac gccgggcctc cccaaa                                        26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
tccaattgtc gacaataaaa ttc                                           23

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
tataacaaga agtcgacagg agaacatatt                                    30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
gtgaagtcga ctgacaattt tggcagtcat c                                  31
```

```
<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
ttattgaagg tcgaccactg ttttgcaacc                                      30

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
aatatgttga cctatggaaa ataatc                                          26

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
gttcgaggtc gacctttgac cgttaattac                                      30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
gttcgaggtc gaccttagac tgttaattac                                      30

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
agtcagaggc gtcgacaata gtgtgc                                          26

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
tataattcat gtcgacgtgt tagtccttcc                                      30

<210> SEQ ID NO 18
```

```
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
agtcactagt agaaaatcta actttggtct ct                                        32

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
cagtgcggcc gcgccggcgt ttgtttgtaa tatagtca                                  38

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
agattttctt cgtatagcag ccac                                                 24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
gtaccatgat atgcatcatt ctctt                                                25

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
gtggctgcta tacgaagaaa atct                                                 24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
acactattat ctacgcctct gact                                                 24

<210> SEQ ID NO 24
<211> LENGTH: 95
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
agtcactagt caaaatttga tattttctc tgttcttaga gttatttctt cacaatgagg      60
ctaattagca caacttctgc aggcggccgc agtca                               95

<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
agtcactagt agaaaatcta actttggttc tctctctcgt tgtcttttcc aacttcaaaa    60
atgaagaatt tgattttcct aacgatgttt ctgactatat tactacaaac aaacgccggc   120
gcggccgcac tg                                                       132
```

The invention claimed is:

1. An isolated nucleic acid promoter comprising a nucleotide sequence for elevating the defensive reaction of a plant against pathogen infection, wherein the nucleic acid promoter comprises SEQ ID NO:1.

2. The nucleic acid promoter according to claim 1, further comprising the nucleotide sequence consisting of SEQ ID NO:24 extending beyond the 3' end of SEQ ID NO:1.

3. A gene construct, which comprises a nucleotide sequence encoding a protein operably linked to a promoter, wherein the protein is a pathogen defense protein and the promoter comprises the nucleic acid promoter according to claim 1.

4. The gene construct according to claim 1, wherein the gene construct enhances local gene expression, which results in direct or indirect antifungal effect.

5. A method for producing a pathogen tolerant plant, said method comprising transforming the genome of a plant with the gene construct acid according to claim 3.

6. A transgenic plant cell comprising the nucleic acid promoter according to claim 1.

7. A transgenic plant, the plant comprising the plant cell according to claim 6.

8. The transgenic plant according to claim 7, wherein the plant is a dicotyledonous plant, and wherein said plant is from a species selected from the group consisting of Fabaceae, Ranunculaceae, Brassicaceae, Chenopodiaceen, Solanaceen, *Lycopersicon, Daucus, Gossypium*, and *Helianthus*.

9. The transgenic plant according to claim 7, wherein said plant is a monocotyledonous plant, and wherein said plant is from a species selected from the group consisting of Poaceae, *Zea mays, Triticum, Avena, Secale*, and *Oryza*.

10. A seed of a transgenic plant comprising a plant cell, wherein said cell comprises a nucleic acid promoter comprising SEQ ID NO:1.

* * * * *